US008791088B2

(12) United States Patent
Bennett et al.

(10) Patent No.: US 8,791,088 B2
(45) Date of Patent: Jul. 29, 2014

(54) COMPOSITIONS AND METHODS FOR MODULATION OF LMNA EXPRESSION

(75) Inventors: C. Frank Bennett, Carlsbad, CA (US); Kenneth W. Dobie, Del Mar, CA (US); Susan M. Freier, San Diego, CA (US); Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/566,922

(22) Filed: Aug. 3, 2012

(65) Prior Publication Data

US 2013/0035370 A1 Feb. 7, 2013

Related U.S. Application Data

(63) Continuation of application No. 12/090,847, filed as application No. PCT/US2006/041018 on Oct. 17, 2006.

(60) Provisional application No. 60/754,517, filed on Dec. 27, 2005, provisional application No. 60/728,709, filed on Oct. 20, 2005.

(51) Int. Cl.
*C12N 15/11* (2006.01)

(52) U.S. Cl.
USPC ........................................................ 514/44 A

(58) Field of Classification Search
USPC ........................................................ 514/44 A
See application file for complete search history.

(56) References Cited

U.S. PATENT DOCUMENTS

| 5,627,274 A | 5/1997 | Kole et al. |
|---|---|---|
| 5,665,593 A | 9/1997 | Kole et al. |
| 5,916,808 A | 6/1999 | Kole et al. |
| 5,976,879 A | 11/1999 | Kole et al. |
| 6,210,892 B1 | 4/2001 | Bennett et al. |
| 7,125,667 B2 | 10/2006 | Blumenfeld et al. |
| 8,258,109 B2 * | 9/2012 | Bennett et al. ............. 514/44 A |
| 2002/0049173 A1 | 4/2002 | Bennett et al. |
| 2004/0009512 A1 | 1/2004 | Ares et al. |
| 2005/0059071 A1 | 3/2005 | Eriksson et al. |

FOREIGN PATENT DOCUMENTS

WO  WO 94/26887  11/1994

OTHER PUBLICATIONS

Applicant's arguments filed Feb. 17, 2011, pp. 1-15, U.S. Appl. No. 12/488,394.*
BPAI decision, U.S. Appl. No. 11/083,583, Appeal No. 2011-009971, Mail date Nov. 28, 2012.*
Cartegni et al., "Correction of disease-associated exon skipping by synthetic exon-specific activators" Nat. Struct. Biol. (2003) 10(2):120-125.
Cartegni et al., "ESEfinder: a web resource to identify exonic splicing enhancers" Nucleic Acids Res. (2003) 31(13):3568-3571.
Eriksson et al., "Recurrent de novo point mutations in lamin a cause Hutchinson-Gilford progeria syndrome" Nature (2003) 423:293-298.
Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.
Harborth et al., "Sequence, Chemical, and Structural Variation of Small Interfering RNAs and Short Hairpin RNAs and the Effect on Mammalian Gene Silencing" Antisense Nucleic Acid Drug Dev. (2003) 13(2):83-105.
Hovhannisyan et al., "A Novel Intronic cis Element, ISE/ISS-3, Regulates Rat Fibroblast Growth Factor Receptor 2 Splicing through Activation of an Upstream Exon and Repression of a Downstream Exon Containing a Noncanonical Branch Point Sequence" Mol. Cell. Biol. (2005) 25(1):250-263.
Huang et al., "Correction of cellular phenotypes of Hutchinson-Gilford Progeria cells by RNA interference" Human Genet. (2005) 118:444-450.
Hutchison et al., "A-type lamins: Guardians of the soma?" Nat. Cell Biol. (2004) 6:1062-1067.
Lacerra et al., "Restoration of hemoglobin A synthesis in erythroid cells from peripheral blood of thalassemic patients" PNAS (2000) 97:9591-9596.
Lin et al., "Structural organization of the human gene encoding nuclear lamin a and nuclear lamin C." J. Biol. Chem. (1993) 268(22):16321-16326.
Minovitsky et al., "The splicing regulatory element, UGCAUG, is phylogenetically and spatially conserved in introns that flank tissue-specific alternative exons" Nucleic Acids Res. (2005) 33(2):714-724.
Mounkes et al., "The A-Type Lamins: Nuclear Structural Proteins as a Focus for Muscular Dystrophy and Cardiovascular Diseases" Trends Cardiovasc. Med. (2001) 11:280-285.
Muchir et al., "The Nuclear Envelope and Human Disease" Physiology (2004) 19:309-314.
Scaffidi e tal., "Reversal of the cellular phenotype in the premature aging disease Hutchinson-Gilford progeria syndrome" Nat. Med. (2005) 11(4):440-445.
Scamborova et al., "An Intronic Enhancer Regulates Splicing of the Twintron of *Drosophila melanogaster* prospero Pre-mRNA by Two Different Spiceosomes" Mol. Cell. Biol. (2004) 24(5):1855-1869.
Taylor et al., "Induction of endogenous Bcl-xS through the control of Bcl-x pre-mRNA splicing by antisense oligonucleotides" Nat. Biotechnol. (1999) 17:1097-1100.
Wang et al., "Distribution of SR protein exonic splicing enhancer motifs in human protein-coding genes" Nucleic Acids Res. (2005) 33(16):5053-5062.

(Continued)

*Primary Examiner* — Brian Whiteman
(74) *Attorney, Agent, or Firm* — Isis Pharmaceuticals, Inc. Patent Dept.

(57) ABSTRACT

Disclosed herein are compounds, compositions and methods for modulating the expression of LMNA in a cell, tissue or animal. Also provided are methods of target validation. Also provided are uses of disclosed compounds and compositions in the manufacture of a medicament for treatment of diseases and disorders. Further provided are methods of identifying cis splicing regulatory elements of a selected mRNA using the disclosed compounds.

18 Claims, No Drawings

(56) References Cited

OTHER PUBLICATIONS

Wilton et al., "Specific removal of the nonsense mutation from the mdx dystrophin mRNA using antisense oligonucleotides" Neuromuscul. Discord. (1999) 9:330-338.

Woolf et al., "Specificity of antisense oligonucleotides in vivo" PNAS (1992) 89:7305-7309.

Wu et al., "Distribution of exonic splicing enhancer elements in human genes" Genomics (2005) 86:329-336.

Yeo et al., "Variation in sequence and organization of splicing regulatory elements in vertebrate genes" Pnas (2004) 101(44):15700-15705.

Young et al., "Prelamin A, Zmpste24, misshapen cell nuclei, and progeria—new evidence suggestingthat protein farnesylation could be important for disease pathogenesis" J. Lipid Res. (2005) 46:2531-2558.

International Search Report for application PCT/US06/41018 dated Jul. 27, 2007.

* cited by examiner

COMPOSITIONS AND METHODS FOR MODULATION OF LMNA EXPRESSION

CROSS-REFERENCE TO RELATED APPLICATIONS

This application is a continuation of U.S. application Ser. No. 12/090,847, filed Aug. 19, 2008, now U.S. Pat. No. 8,258,109, which is a National Stage application filed under 35 U.S.C. 371 of International Application No. PCT/US2006/041018, filed Oct. 17, 2006, which claims the priority under 35 U.S.C. 119(e) to U.S. provisional patent application Ser. No. 60/754,517, filed Dec. 27, 2005, and U.S. provisional patent application Ser. No. 60/728,709, filed Oct. 20, 2005. Each of the above applications is incorporated by reference in their entirety.

SEQUENCE LISTING

The present application is being filed along with a Sequence Listing in electronic format. The Sequence Listing is provided as a file entitled CORE0064USC1SEQ.txt, created Aug. 3, 2012, which is 80 kb in size. The information in the electronic format of the sequence listing is incorporated herein by reference in its entirety.

BACKGROUND

The LMNA gene encodes two alternatively spliced products, lamin A and lamin C (Lin and Worman, 1993, *J. Biol. Chem.* 268:16321-16326). The N-terminal 566 amino acids of lamin A and lamin C are identical with lamin C containing 6 unique amino acids at the C-terminus to yield a protein of 572 amino acids. Lamin A, which is 646 amino acids in length, is generated from a precursor protein, prelamin A, by a series of posttranslational processing steps (Young et al., 2005, *J. Lipid Res. Oct* 5 electronic publication). The first step in prelamin A processing is farnesylation of a carboxyl-terminal cysteine residue, which is part of a CAAX motif at the terminus of the protein. Next, the terminal three amino acids (AAX) are cleaved from the protein, after which the farnesylcysteine is methylated. Finally, the C-terminal 15 amino acids are enzymatically removed and degraded to form mature lamin A.

Lamin A and lamin C are key structural components of the nuclear lamina, an intermediate filament meshwork underneath the inner nuclear membrane. The lamin proteins comprise N-terminal globular head domains, central helical rod domains and C-terminal globular tail domains. Lamins A and C homodimerize to form parallel coiled-coil dimers, which associate head-to-tail to form strings, and ultimately form the higher-order filamentous meshwork that provides structural support for the nucleus (Muchir and Worman, 2004, *Physiology (Bethesda)* 19:309-314; Mutchison and Worman, 2004, *Nat. Cell Biol.* 6:1062-1067; Mounkes et al. 2001, *Trends Cardiovasc. Med.* 11:280-285).

Hutchinson-Gilford progeria syndrome (HGPS) is a childhood premature aging disease resulting from the production of a mutant form of farnesyl-prelamin A, which cannot be processed to mature lamin A. The accumulation of farnesyl-prelamin A is toxic, inducing misshapen nuclei at the cellular level and a wide range of disease symptoms at the organismal level (e.g., osteoporosis, alopecia, micrognathia and dental abnormalities). HGPS is most commonly caused by a spontaneous mutation in exon 11 of LMNA, which activates a cryptic splice site four nucleotides upstream of the mutation (a cytosine to thymidine substitution at codon 608) (Eriksson et al. 2003, *Nature* 423:293-298). The pre-mRNA derived from the mutated allele is spliced using the aberrant donor splice site and the correct exon 12 acceptor site, yielding a truncated LMNA mRNA lacking the terminal 150 nucleotides of exon 11. As a result of aberrant splicing, a mutant protein lacking 50 amino acids from the globular tail is produced.

Antisense compounds targeting a selected mRNA or pre-mRNA molecule have proven effective at either reducing total levels of target mRNA through target degradation, or altering the ratio of specific target splice products through occupancy-based mechanisms. Given the role of LMNA in diseases such as HGPS, methods of reducing expression of LMNA mRNA or methods of modulating splicing of LMNA pre-mRNA to eliminate expression of mutant lamin A protein are needed.

A method of controlling the behavior of a cell through modulation of the processing of an mRNA target by contacting the cell with an antisense compound acting via a non-cleavage event is disclosed in U.S. Pat. No. 6,210,892 and U.S. Pre-Grant Publication 2002-0049173.

Kole et al. (WO 94/26887 and U.S. Pat. Nos. 5,627,274; 5,916,808; 5,976,879; and 5,665,593) disclose methods of combating aberrant splicing using modified antisense oligonucleotides which do not activate RNase H.

Scaffidi and Misteli (2005, *Nat. Med.* 11(4):440-445) disclose a morpholino oligonucleotide used to correct aberrant splicing of LMNA in HGPS fibroblasts.

U.S. Pre-Grant Publication 2005-0059071 discloses mutations in the LMNA gene that cause HGPS and methods of influencing expression of LMNA. Such methods include the use of oligonucleotides and other compounds.

Huang et al. (2005, *Human Genet.*, Oct 6, electronic publication) discuss short hairpin RNA (shRNA) constructs designed to target mutant LMNA pre-mRNA or mature LMNA mRNA to decrease expression of mutant lamin A protein.

Harborth et al. (2003, *Antisense Nucleic Acid Drug Dev.* 13(2):83-105) discuss LMNA gene silencing using siRNA compounds.

Antisense technology is an effective means for reducing the expression of one or more specific gene products and is uniquely useful in a number of therapeutic, diagnostic, and research applications. Provided herein are antisense compounds for use in modulation of LMNA expression, either through RNase H-dependent cleavage, or by modulation of LMNA splicing. Also provided herein is a method for identifying cis splicing regulatory elements of a selected pre-mRNA, such as LMNA pre-mRNA.

SUMMARY

Provided herein are antisense compounds targeted to LMNA which specifically hybridize with and inhibit expression of LMNA. In one embodiment, the antisense compounds comprise at least one 2'-O-(2-methoxyethyl) nucleotide. Preferred antisense compounds are antisense oligonucleotides. In one embodiment, the antisense oligonucleotides provided herein comprise at least one modified internucleoside linkage. Also provided are antisense oligonucleotides comprising modified internucleoside linkages at each position. In one aspect, the modified internucleoside linkage is phosphorothioate. In one embodiment, the antisense oligonucleotides comprise at least one modified nucleobase. In one aspect, the modified nucleobase is 5-methylcytosine.

Further provided are chimeric antisense oligonucleotides targeted to LMNA. In one embodiment, the chimeric antisense oligonucleotides comprise a first region with one or more deoxynucleotides and second and third regions flanking said first region, each with at least one 2'-O-(2-methoxyethyl) nucleotide. In one aspect, the first region contains 10 nucleotides and each of the second and third regions contain 5 nucleotides. The chimeric antisense oligonucleotides provided herein can further comprise modified internucleoside linkages and/or modified nucleobases.

Also provided herein are pharmaceutical compositions comprising the antisense compounds and a pharmaceutically acceptable penetration enhancer, carrier or diluent.

Methods of inhibiting expression of LMNA in cells or tissues by contacting the cells or tissues with the antisense compounds described herein are also provided.

Also provided herein are antisense oligonucleotides targeted to LMNA pre-mRNA which specifically hybridize with and modulate processing of LMNA. In one embodiment, the antisense oligonucleotides comprise a modified sugar residue at each nucleotide. In one aspect, the modified sugar moiety is 2'-O-(2-methoxyethyl). In another embodiment, the antisense oligonucleotides that modulate processing comprise a modified internucleoside linkage at each position. In another embodiment, each cytosine of the antisense oligonucleotide is replaced with 5-methylcytosine. In one aspect, the modulation of processing is modulation of splicing. In one embodiment, the antisense oligonucleotides are targeted to intron:exon, exon:intron or exon:exon junctions. In another embodiment, the antisense oligonucleotides target a splice site. Splice sites include, but are not limited to, splice acceptor sites, splice donor sites, constitutive splice sites, cryptic splice sites and aberrant splice sites. In another embodiment, the antisense oligonucleotides target cis splicing regulatory elements. Regulatory elements include, but are not limited to, intronic splicing enhancers, intronic splicing silencers, exonic splicing enhancers and exonic splicing silencers. In another embodiment, the antisense oligonucleotides target exon 11 of LMNA. In one aspect, the antisense oligonucleotides that modulate splicing target a nucleic acid encoding LMNA which comprises a point mutation in exon 11. The point mutation can be a C to T substitution in codon 608.

Further provided are methods of modulating splicing of LMNA pre-mRNA by contacting cells or tissues with one or more of the antisense compounds. In one embodiment, the modulation of splicing results in an increase in the ratio of full-length LMNA mRNA to truncated LMNA mRNA. In another embodiment, the modulation of splicing results in an increase in the ratio of full-length lamin A protein to truncated lamin A protein.

Provided herein is a method for identifying cis splicing regulatory elements of a selected pre-mRNA by selecting a splice site of the pre-mRNA, designing a set of antisense compounds targeting a region up to about 500, up to about 250, up to about 150, or up to about 75 nucleotides 5' (upstream) or 3' (downstream) of the selected splice site and screening the antisense compounds to identify compounds that modulate the ratio of splicing products of the pre-mRNA. The compounds used in the methods provided herein do not elicit RNase H mediated degradation of the target nucleic acid. These compounds are termed "RNase H-independent" compounds. In one embodiment, the cis regulatory element is a splicing silencer element. In another embodiment, the cis regulatory element is a splicing enhancer element. An increase in usage of the selected splice site upon binding of the antisense compound indicates identification of a splicing silencer element and a decrease in usage of the selected splice site indicates identification of a splicing enhancer element.

The antisense compounds designed for identification of cis splicing regulatory elements can target splice acceptor sites, splice donor sites, constitutive splice sites, cryptic splice sites or aberrant splice sites. The cis regulatory element can be in an intron or an exon. In some embodiments, the antisense compounds of the method are 12 to 30 nucleobases in length. In other embodiments, the antisense compounds of the method are 16 to 20 nucleobases in length.

In one embodiment, the RNase H-independent compounds provided herein for the method of identifying cis regulatory elements comprise at least one modified nucleotide. In one embodiment, the antisense compounds comprise a modified nucleotide at each position. In a further embodiment, the antisense compounds comprise uniformly modified nucleotides. In one embodiment, the modified nucleotide or nucleotides comprise a sugar modification. In one aspect, the sugar modification is 2'-O-methoxyethyl. In another aspect, the antisense compounds further comprise phosphorothioate linkages at each position. In one embodiment, the antisense compounds comprise at least one mimetic. In one aspect, the mimetic is a peptide nucleic acid. In another aspect, the mimetic is a morpholino group.

Also provided is the use of an antisense oligonucleotide targeted to human LMNA for the preparation of a medicament for the inhibition of LMNA in a cell or tissue. Further provided is the use of a fully modified antisense oligonucleotide for the preparation of a medicament for modulation of splicing of LMNA in a cell or tissue. The use of an antisense oligonucleotide targeted to human LMNA for the preparation of a medicament for the treatment of HGPS is also provided.

DETAILED DESCRIPTION

Antisense technology is an effective means for reducing the expression of one or more specific gene products and is uniquely useful in a number of therapeutic, diagnostic, and research applications. Provided herein are antisense compounds useful for modulating gene expression and associated pathways via antisense mechanisms of action based on target degradation or target occupancy. Also provided herein are antisense compounds useful for identification of cis splicing regulatory elements present in pre-mRNA molecules, including exonic splicing enhancers, exonic splicing silencers, intronic splicing enhancers and intronic splicing silencers.

The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

The role of LMNA in diseases such as HGPS makes it an important therapeutic target. Both LMNA mRNA target knockdown and modulation of LMNA splice product ratios are desirable outcomes. Thus, provided herein are two types of antisense compounds targeting LMNA. One type of antisense compound targets LMNA and results in target degradation. The second type of compound targets specific components of LMNA pre-mRNA to modulate splicing. The latter compounds do not elicit RNase H-dependent degradation of the target (RNase H-independent compounds). Modulation of splicing is used to alter the ratio of splicing products to increase the desired splice product and decrease the undesired splice product. In the case of LMNA nucleic acids containing mutations in exon 11, which lead to development of HGPS, oligomeric compounds are designed to block splicing from a cryptic splice site activated by the mutation in exon 11. In one aspect, the antisense compounds target splicing elements, such as splicing enhancer elements or splicing silencer elements. The enhancer elements and silencer elements can be found in introns or exons.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (ISS) have been identified which either repress or enhance usage of splice donor sites or splice acceptor sites, depending on their site and mode of action (Yeo et al. 2004, *Proc. Natl. Acad. Sci. U.S.A.* 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, *Mol. Cell. Biol.* 24(5):1855-1869; Hovhannisyan and Carstens, 2005, *Mol. Cell. Biol.* 25(1):250-263; Minovitsky et al. 2005, *Nucleic Acids Res.* 33(2):714-724). Little is known about the trans factors that interact with intronic splicing elements; however, a number of studies have provided information on exonic splicing elements. For example, ESEs are known to be involved in both alternative and constitutive splicing by acting as binding sites for members of the SR protein family. SR proteins bind to splicing elements via their RNA-binding domain and promote splicing by recruiting spliceosomal components with protein-protein interactions mediated by their RS domain, which is comprised of several Arg-Ser dipeptides (Cartegni and Krainer, 2003, *Nat. Struct. Biol.* 10(2):120-125; Wang et al. 2005, *Nucleic Acids Res.* 33(16):5053-5062). ESEs have been found to be enriched in regions of exons that are close to splice sites, particularly 80 to 120 bases from the ends of splice acceptor sites (Wu et al. 2005, *Genomics* 86:329-336). Consensus sequences have been determined for four members of the SR protein family, SF2/ASF, SC35, SRp40 and SRp55 (Cartegni et al. 2003, *Nucleic Acids Res.* 31(13):3568-3571). Although the trans factors that bind intronic splicing regulatory elements have not been extensively studied, SR proteins and heterogeneous ribonucleoproteins (hnRNPs) have both been suggested to interact with these elements (Yeo et al. 2004, *Proc. Natl. Acad. Sci. U.S.A.* 101(44):15700-15705).

Identification of splicing enhancer and splicing silencer elements would be of great value for identification of therapeutic tools useful for modulating splicing. Thus, provided herein are methods of identifying splicing elements using modified antisense compounds. It is shown herein that splicing elements can be identified by designing a series of modified antisense compounds targeting a region of a gene of interest, particularly targeting regions up to about 500 nucleotides upstream (5') or downstream (3') of a selected pre-mRNA splice site. Antisense compounds also can be targeted to regions up to about 250, or up to about 150, or up to about 75 nucleotides upstream or downstream of a selected pre-mRNA splice site. The splice sites can be splice donor sites (also known as 5' splice sites) or splice acceptor sites (also known as 3' splice sites). Furthermore, the splice sites can be constitutive (normal) splice sites or they can be cryptic or aberrant splice sites. The modified antisense compounds are RNase H-independent and thus function by occupancy-based mechanisms. The antisense compounds are then screened in an appropriate in vitro, ex vivo or in vivo system to identify compounds that alter the ratio of splicing products of the selected pre-mRNA. Methods of screening antisense compounds are well known in the art. For example, an antisense compound targeting a region upstream of a normal splice site which is found to enhance splicing of an alternative transcript suggests the compound binds to a splicing enhancer element for the normal (constitutive) splice product. Alternatively, an antisense compound targeting a region upstream of a normal splice site which is found to enhance splicing of the normal transcript suggests the compound binds to a splicing silencer element for the normal splice product. The same logic is applied to antisense compounds targeting regions upstream of a cryptic, or alternative, splice site. The splicing regulatory elements can be in exons or introns. While not wishing to be bound by theory, the modified antisense compounds targeting splicing regulatory elements may function by blocking trans regulatory factors such as SR proteins or hnRNPs from binding the splicing regulatory elements, which would alter recruitment of spliceosomal components that regulate splice site selection and usage.

Identification of splicing elements for LMNA is illustrated herein; however, the methods provided herein can be used to identify cis splicing regulatory elements of any known pre-mRNA having at least one alternative splice product. The methods provided herein are particularly useful for identifying splicing regulatory elements for genes associated with genetic diseases, particularly those that result from alterations in splicing. Up to 50% of point mutations linked to genetic diseases in humans result in aberrant splicing. Such point mutations can alter splicing by directly inactivating or creating a splice site, indirectly activating a cryptic splice site or interfering with regulatory cis elements (Cartegni and Krainer, 2003, *Nat. Struct. Biol.* 10(2):120-125). Antisense oligonucleotides have been used to block cryptic splice sites, which were activated by mutations that inhibit use of the normal splice sites, for both human β-globin and CFTR (Lacerra et al. 2000, *Proc. Natl. Acad. Sci. U.S.A.* 97:9591-9596; Frieman et al. 1999, *J. Biol. Chem.* 274:36193-36199). Similarly, antisense oligonucleotides have been used to modulate splicing of Bcl-x to favor either the short form or the long form (Taylor et al. 1999, *Nat. Biotechnol.* 17:1097-1100) and to force skipping of a specific dystrophin exon harboring a premature termination codon (Wilton et al. 1999, *Neuromuscul. Disord.* 9:330-338).

As used herein, the terms "target nucleic acid" and "nucleic acid molecule encoding LMNA" have been used for convenience to encompass DNA encoding LMNA, RNA (including pre-mRNA and mRNA or portions thereof) transcribed from such DNA, and also cDNA derived from such RNA.

As used herein, "targeting" or "targeted to" refer to the process of designing an oligomeric compound such that the compound hybridizes with a selected nucleic acid molecule or portion of a selected nucleic acid molecule.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences.

As used herein, "antisense mechanisms" are all those involving hybridization of a compound with target nucleic acid, wherein the outcome or effect of the hybridization is either target degradation or target occupancy with concomitant stalling of the cellular machinery involving, for example, translation or splicing.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art.

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and mRNA. In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated. In the context of the present disclosure, an antisense compound targeting a region up to about 500 nucleobases upstream (5') or downstream (3') of a splice site refers to a compound that hybridizes with at least a portion of an intron or exon sequence that is 0 to 500 nucleobases upstream or downstream of the splice site As used herein "splice donor site" refers to a splice site found at the 5' end of an intron. Splice donor site is used interchangeably with "5' splice site." As used herein "splice acceptor site" refers to a splice site found at the 3' end of an intron. Splice acceptor site is used interchangeably with "3' splice site."

As used herein, usage of a splice site refers to the cellular spliceosomal machinery recognizing and selecting a particular splice site during the splicing process such that the spliced mRNA product reflects use of that site as either a splice donor site or a splice acceptor site. In the context of the present disclosure, if usage of a particular splice site is favored (such as by treatment with one of the antisense compounds provided herein) over a second splice site, the ratio of mRNA products resulting from the splicing reaction will be altered. One of skill in the art is able to determine the splice sites of a selected pre-mRNA and predict the size and nature of the possible splicing products and thus determine which splice sites are being used under a given condition. For example, in the context of the present disclosure, an antisense compound that causes an increase in usage of a selected splice site indicates the compound is interfering with a splicing silencer element and an antisense compound that causes a decrease in usage of the selected splice site indicates the compound is interfering with a splicing enhancer element. Thus, the antisense compounds provided herein are useful for identifying the presence of splicing enhancer and splicing silencer elements by assessing the ratio of splicing products.

As used herein, "cis splicing regulatory elements" are regions of sequence found in a pre-mRNA molecule which modulate splicing of the mRNA. These regulatory elements are presumed to function through interaction with trans factors that either positively or negatively regulate the cellular spliceosomal machinery. Cis splicing regulatory elements include splicing enhancers and splicing silencers. Splicing enhancers present in exons are termed "exonic splicing enhancers" or "ESEs" and splicing enhancers present in introns are termed "intronic splicing enhancers" or "ISEs." Similarly, splicing silencers present in exons are termed "exonic splicing silencers" or "ESSs" and splicing silencers present in introns are termed "intronic splice silencers" or "ISSs."

As used herein, "RNase H-independent" compounds are antisense compounds having a least one chemical modification such that when the compound is bound to a target nucleic acid, the modification increases resistance of the target nucleic acid to RNase H-mediated cleavage. Such modifications include, but are not limited to, nucleotides with modified sugar moieties. As used herein, nucleotides with modified sugar moieties include, but are not limited to, any nucleotide wherein the 2'-deoxyribose sugar has been substituted with a chemically modified sugar moiety. In the context of the present disclosure, chemically modified sugar moieties include, but are not limited to, 2'-O-(2-methoxyethyl), 2'-fluoro, 2'-dimethylaminooxyethoxy, 2'-dimethylaminoethoxyethyl, 2'-guanidinium, 2'-O-guanidinium ethyl, 2'-carbamate, 2'-aminooxy, 2'-acetamido, and bicyclic nucleic acids. Modified compounds that confer resistance to RNase H-mediated target cleavage are thoroughly described herein and are well known in the art.

As used herein, "uniformly modified" refers to antisense compounds wherein each nucleotide comprises the same modification or modifications.

As used herein, "Bicyclic nucleic acids" or "BNAs" refer to nucleic acids which have a modified ribofuranosyl moiety wherein two non-geminal ring carbon atoms are bridged. Exemplary BNAs which are useful in the context of the present disclosure are BNAs which have a bridge between the 4' and the 2' position of the ribofuranosyl moiety, such as, for example, methyleneoxy (4'-CH2-O-2') BNA and ethyleneoxy (4'-CH2CH2-O-2') BNA.

Target Nucleic Acids

As used herein, "targeting" or "targeted to" refer to the process of designing an oligomeric compound such that the compound hybridizes with a selected nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding LMNA" encompass DNA encoding LMNA, RNA (including pre-mRNA and mRNA) transcribed from such DNA, and also cDNA derived from such RNA. As disclosed herein, the target nucleic acid encodes LMNA.

The targeting process usually also includes determination of at least one target region, segment, or site within the target nucleic acid for the antisense interaction to occur such that the desired effect (e.g., modulation of expression) will result. "Region" is defined as a portion of the target nucleic acid having at least one identifiable structure, function, or characteristic. Target regions may include, for example, a particular exon or intron, or may include only selected nucleobases within an exon or intron which are identified as appropriate target regions. Within regions of target nucleic acids are segments. "Segments" are defined as smaller or sub-portions of regions within a target nucleic acid. "Sites," as used herein, are defined as unique nucleobase positions within a target nucleic acid. As used herein, the "target site" of an oligomeric compound is the 5'-most nucleotide of the target nucleic acid to which the compound binds.

Provided herein are compositions and methods for modulating the expression of LMNA (also known as EMD2; FPL; FPLD; LDP1; LFP; LMN1; lamin A; lamin A/C; lamin C; nuclear envelope protein lamin A precursor; nuclear envelope protein lamin C precursor). Listed in Table 1 are GENBANK® accession numbers of sequences used to design antisense compounds targeted to LMNA. Antisense compounds include compounds which hybridize with one or more target nucleic acid molecules shown in Table 1, as well as antisense compounds which hybridize to other nucleic acid molecules encoding LMNA. The antisense compounds may target any region, segment, or site of nucleic acid molecules which encode LMNA. Suitable target regions, segments, and sites include, but are not limited to, the 5'UTR, the start codon, the stop codon, the coding region, the 3'UTR, the 5'cap region, introns, exons, intron-exon junctions, exon-intron junctions, exon-exon junctions, splice sites and splicing regulatory elements.

TABLE 1

LMNA Target Sequences

| Target Name | Species | Genbank ® # | SEQ ID NO |
|---|---|---|---|
| LMNA | Human | AY357727.1 | 1 |
| LMNA | Human | BC014507.1 | 2 |
| LMNA | Human | NM_005572.2 | 3 |
| LMNA | Human | NM_170707.1 | 4 |
| LMNA | Human | NM_170708.1 | 5 |
| LMNA | Human | NM_170717.1 | 6 |
| LMNA | Human | nucleotides 2533930 to 2560103 of NT_079484.1 | 7 |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of LMNA. Thus, in one embodiment modulation of expression can mean increase or decrease in target RNA or protein levels. In another embodiment modulation of expression can mean an increase or decrease of one or more RNA splice products, or a change in the ratio of two or more splice products.

Modulation of LMNA expression can be assayed in a variety of ways known in the art. LMNA mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Levels of a protein encoded by LMNA can be quantitated in a variety of ways well known in the art, such as immunoprecipitation, Western blot analysis (immunoblotting), ELISA or fluorescence-activated cell sorting (FACS).

Kits, Research Reagents and Diagnostics

The antisense compounds provided herein can be utilized for diagnostics, and as research reagents and kits. Furthermore, antisense compounds, which are able to inhibit gene expression or modulate gene expression with specificity, are often used by those of ordinary skill to elucidate the function of particular genes or to distinguish between functions of various members of a biological pathway.

For use in kits and diagnostics, the antisense compounds provided herein, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Therapeutics

Antisense compounds provided herein can be used to modulate the expression of LMNA in an animal, such as a human. In one non-limiting embodiment, the methods comprise the step of administering to said animal in need of therapy for a disease or condition associated with LMNA an effective amount of an antisense compound that modulates expression of LMNA. A disease or condition associated with LMNA includes, but is not limited to, HGPS. Antisense compounds that effectively modulate expression of LMNA RNA or protein products of expression are considered active antisense compounds.

For example, modulation of expression of LMNA can be measured in a bodily fluid, which may or may not contain cells; tissue; or organ of the animal. Methods of obtaining samples for analysis, such as body fluids (e.g., sputum, serum), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of inflammation.

The antisense compounds provided herein can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. The compounds provided herein can also be used in the manufacture of a medicament for the treatment of diseases and disorders related to LMNA.

Methods whereby bodily fluids, organs or tissues are contacted with an effective amount of one or more of the antisense compounds or compositions are also contemplated. Bodily fluids, organs or tissues can be contacted with one or more of the compounds described herein resulting in modulation of LMNA expression in the cells of bodily fluids, organs or tissues. An effective amount can be determined by monitoring the modulatory effect of the antisense compound or compounds or compositions on target nucleic acids or their products by methods routine in the art.

Thus, provided herein is the use of an antisense compound targeted to LMNA in the manufacture of a medicament for the treatment of a disease or disorder by means of the method described above.

Antisense Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Nonlimiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds comprise compounds from 8 to 80 nucleobases (i.e. from 8 to 80 linked nucleosides). One will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds comprise 13 to 80 nucleobases. One will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds comprise 12 to 50 nucleobases. One will appreciate that this embodies antisense compounds of 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds comprise 12 to 30 nucleobases. One will appreciate that this embodies antisense compounds of 12, 13, 14, 15, 16, 17, 18, 19, 20, 21, 22, 23, 24, 25, 26, 27, 28, 29 or 30 nucleobases.

In some embodiments, the antisense compounds comprise 15 to 30 nucleobases. One will appreciate that this embodies antisense compounds of 15, 16, 17, 18, 19, 20, 21, 22, 23, 24, 25, 26, 27, 28, 29 or 30 nucleobases.

In one embodiment, the antisense compounds comprise 20 to 30 nucleobases. One will appreciate that this embodies antisense compounds of 20, 21, 22, 23, 24, 25, 26, 27, 28, 29, or 30 nucleobases.

In one embodiment, the antisense compounds comprise 20 to 24 nucleobases. One will appreciate that this embodies antisense compounds of 20, 21, 22, 23, or 24 nucleobases.

In one embodiment, the antisense compounds comprise 16 to 20 nucleobases. One will appreciate that this embodies antisense compounds of 16, 17, 18, 19 or 20 nucleobases.

In one embodiment, the antisense compounds comprise 20 nucleobases.

In one embodiment, the antisense compounds comprise 19 nucleobases.

In one embodiment, the antisense compounds comprise 18 nucleobases.

In one embodiment, the antisense compounds comprise 17 nucleobases.

In one embodiment, the antisense compounds comprise 16 nucleobases.

In one embodiment, the antisense compounds comprise 15 nucleobases.

In one embodiment, the antisense compounds comprise 14 nucleobases.

In one embodiment, the antisense compounds comprise 13 nucleobases.

Antisense compounds 8-80 nucleobases in length, or any length within the recited range, comprising a stretch of at least eight (8) consecutive nucleobases selected from within the illustrative antisense compounds are considered to be suitable antisense compounds.

Compounds provided herein include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains 8 to 80, or 13 to 80, or 12 to 50, or 12 to 30, or 15 to 30, or 20 to 30, or 20 to 24, or 16 to 20 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains 8 to 80, or 13 to 80, or 12 to 50, or 12 to 30, or 15 to 30, or 20 to 30, or 20 to 24, or 16 to 20 nucleobases.

Validated Target Segments

The locations on the target nucleic acid to which active oligomeric compounds hybridize are herein below referred to as "validated target segments." As used herein the term "validated target segment" is defined as at least an 8-nucleobase portion (i.e. 8 consecutive nucleobases) of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80 nucleobases). Similarly validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 to about 80 nucleobases.

The validated target segments identified herein can be employed in a screen for additional compounds that modulate the expression of LMNA. "Modulators" are those compounds that modulate the expression of LMNA and which comprise at least an 8-nucleobase portion (i.e. 8 consecutive nucleobases) which is complementary to a validated target segment. The screening method comprises the steps of contacting a validated target segment of a nucleic acid molecule encoding LMNA with one or more candidate modulators, and selecting for one or more candidate modulators which perturb the expression of a nucleic acid molecule encoding LMNA. Once it is shown that the candidate modulator or modulators are capable of modulating the expression of a nucleic acid molecule encoding LMNA, the modulator can then be employed in further investigative studies of the function of LMNA, or for use as a research, diagnostic, or therapeutic agent. Modulator compounds of LMNA can also be identified or further investigated using one or more phenotypic assays, each having measurable endpoints predictive of efficacy in the treatment of a particular disease state or condition. Phenotypic assays, kits and reagents for their use are well known to those skilled in the art.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Complementarity

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds provided herein comprise at least 70%, or at least 75%, or at least 80%, or at least 85%, or at least 90%, or at least 95%, or at least 96%, or at least 97%, or at least 98%, or at least 99% sequence complementarity to a target nucleic acid sequence. For example, an oligomeric compound in which 18 of 20 nucleobases of the antisense compound are complementary to a target nucleic acid, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the compounds provided herein. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489).
Identity Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences would be considered identical as they both pair with adenine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original, or first, sequence present in a portion of the modified, or second, sequence. In a preferred embodiment, the oligonucleotides are at least about 80%, at least about 85%, at least about 90%, at least about 95% or 100% identical to at least a portion of one of the illustrated antisense compounds, or of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs. It is understood that antisense compounds can vary in length and percent complementarity to the target provided that they maintain the desired activity. Methods to determine desired activity are disclosed herein and well known to those skilled in the art.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the compounds described herein. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of modified sugars includes but is not limited to bicyclic modified sugars (BNA's), including methyleneoxy (4'-CH2-O-2') BNA and ethyleneoxy (4'-CH2CH2-O-2') BNA; and substituted sugars, especially 2'-substituted sugars having a 2'-F, 2'-$OCH_2$ or a 2'-O($CH_2$)$_2$—$OCH_3$ substituent group. Sugars can also be replaced with sugar mimetic groups among others. Methods for the preparations of modified sugars are well known to those skilled in the art. In the context of the present disclosure, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, methyleneoxy (4'-CH2-O-2') BNA and ethyleneoxy (4'-CH2CH2-O-2') BNA.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)2-O—); and N,N'-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorus-containing and non-phosphorus-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

As used herein, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present disclosure provides compounds having reactive phosphorus groups useful for forming internucleoside linkages including for example phosphodiester and phosphorothioate internucleoside linkages. Methods of preparation and/or purification of precursors or antisense compounds are not a limitation of the compositions or methods provided herein. Methods for synthesis and purification of DNA, RNA, and the antisense compounds provided herein are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

As used herein, the term "fully modified motif" refers to an antisense compound comprising a contiguous sequence of nucleosides wherein essentially each nucleoside is a sugar modified nucleoside having uniform modification.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present disclosure is meant to include all such possible isomers, as well as their racemic and optically pure forms.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Oligomer Purification and Analysis

Methods of oligonucleotide purification and analysis are known in the art. Analysis methods include capillary electrophoresis (CE) and electrospray-mass spectroscopy. Such synthesis and analysis methods can be performed in multi-well plates. The methods described herein are not limited by the method of oligomer purification.

Salts, Prodrugs and Bioequivalents

The antisense compounds described herein comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions provided herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

NONLIMITING DISCLOSURE AND INCORPORATION BY REFERENCE

While certain compounds, compositions and methods have been described herein with specificity in accordance with certain embodiments, the following examples serve only to illustrate the disclosed compounds and are not intended to limit the same. Each of the references, GENBANK® accession numbers, and the like recited in the present application is incorporated herein by reference in its entirety.

EXAMPLE 1

Cell Culture and Treatment with Oligomeric Compounds

The effect of oligomeric compounds on target nucleic acid expression was tested in A549 or T24 cells. The human lung carcinoma cell line A549 was obtained from the American Type Culture Collection (Manassas, Va.). A549 cells are routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells are routinely passaged by trypsinization and dilution when they reached approximately 90% confluence. Cells are seeded into 96-well plates (Falcon-Primaria #3872) at a density of approximately 5000 cells/well for use in oligomeric compound transfection experiments.

The transitional cell bladder carcinoma cell line T24 was obtained from the American Type Culture Collection (ATCC) (Manassas, Va.). T24 cells are routinely cultured in complete McCoy's 5A basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 µg/mL (Invitrogen Life Technologies, Carlsbad, Calif.). Cells are routinely passaged by trypsinization and dilution when they reach 90% confluence. Cells are seeded into 96-well plates (Falcon-Primaria #3872) at a density of 7000 cells/well for treatment with the antisense compound.

When cells reach appropriate confluency, they are treated with oligonucleotide using Lipofectin™ as described. When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Control oligonucleotides are used to determine the optimal oligomeric compound concentration for a particular cell line. Furthermore, when oligomeric compounds are tested in oligomeric compound screening experiments or phenotypic assays, control oligonucleotides are tested in parallel. The concentration of oligonucleotide used varies from cell line to cell line.

primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

Probes and primers for use in real-time PCR were designed to hybridize to target-specific sequences. The primers and probes and LMNA target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

LMNA-specific primers and probes for use in real-time PCR

| Target Name | Species | Target SEQ ID NO | Sequence Description | Sequence (5' to 3') | SEQ ID NO |
|---|---|---|---|---|---|
| LMNA | Human | 4 | Forward Primer | CCTTAAAACCAAAGAGGGCTTC | 8 |
| LMNA | Human | 4 | Reverse Primer | CATGTCACAGGGTCCCCG | 9 |
| LMNA | Human | 4 | Probe | CTTTTCTGCCCTGGCTGCTGCC | 10 |

EXAMPLE 2

Real-Time Quantitative PCR Analysis of LMNA mRNA Levels

Quantitation of LMNA mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse

EXAMPLE 3

Antisense Inhibition of Human LMNA by Oligomeric Compounds

A series of oligomeric compounds was designed to target different regions of human LMNA, using published sequences cited in Table 1. The compounds are shown in Table 3. All compounds in Table 3 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were screened for their modulatory effect on LMNA mRNA levels by quantitative real-time PCR as described in other examples herein. Data are averages from experiments in which A549 cells were treated with the antisense compounds at a concentration of 75 nM. Data are expressed as percent inhibition relative to control-treated cells.

TABLE 3

Inhibition of human LMNA mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 366687 | 1 | 2001 | GGGCTCTGGGCTCCTGAGCC | 3 | 11 |
| 366773 | 4 | 1913 | CCGAGCTGCTGCAGTGGGAG | 42 | 12 |
| 366774 | 4 | 1966 | GCAGGTCCCGCACAGCACGG | 61 | 13 |
| 366775 | 4 | 1994 | TGGCAGATGCCTTGTCGGCA | 21 | 14 |
| 366776 | 4 | 2001 | GAGCCGCTGGCAGATGCCTT | 24 | 15 |
| 366777 | 4 | 2003 | CTGAGCCGCTGGCAGATGCC | 60 | 16 |
| 366778 | 4 | 2030 | AGGAGATGGGTCCGCCCACC | 44 | 17 |
| 366779 | 4 | 2033 | CAGAGGAGATGGGTCCGCCC | 38 | 18 |
| 366780 | 4 | 2035 | GCCAGAGGAGATGGGTCCGC | 54 | 19 |
| 366781 | 4 | 2037 | GAGCCAGAGGAGATGGGTCC | 43 | 20 |
| 359381 | 4 | 2048 | TGGAGGCAGAAGAGCCAGAG | 50 | 21 |
| 366782 | 4 | 2052 | ACACTGGAGGCAGAAGAGCC | 43 | 22 |
| 366783 | 4 | 2054 | TGACACTGGAGGCAGAAGAG | 44 | 23 |
| 366784 | 4 | 2057 | CCGTGACACTGGAGGCAGAA | 47 | 24 |
| 366785 | 4 | 2062 | AGTGACCGTGACACTGGAGG | 69 | 25 |
| 366786 | 4 | 2067 | CTGCGAGTGACCGTGACACT | 67 | 26 |
| 366787 | 4 | 2072 | GGTAGCTGCGAGTGACCGTG | 71 | 27 |
| 366788 | 4 | 2162 | TCTGGGTTCGGGGCTGGAG | 54 | 28 |
| 366789 | 4 | 2165 | GGCTCTGGGTTCGGGGCTG | 3 | 29 |
| 366686 | 4 | 2166 | GGGCTCTGGGTTCGGGGCT | 13 | 30 |
| 366685 | 4 | 2171 | TCTGGGGCTCTGGGTTCGG | 15 | 31 |
| 366790 | 4 | 2174 | AGTTCTGGGGCTCTGGGTT | 0 | 32 |
| 366791 | 4 | 2178 | CTGCAGTTCTGGGGCTCTG | 38 | 33 |
| 366792 | 4 | 2193 | CCAGATTACATGATGCTGCA | 75 | 34 |
| 366793 | 4 | 2202 | TGGCAGGTCCCAGATTACAT | 73 | 35 |
| 366794 | 4 | 2462 | TTTCCTGGAAGCAGGGAAAA | 41 | 36 |
| 366795 | 4 | 2491 | CCCTCTTTGGTTTTAAGGCA | 81 | 37 |
| 366796 | 4 | 2502 | TCTAGAGGAAGCCCTCTTTG | 45 | 38 |
| 366797 | 4 | 2507 | TGGCTTCTAGAGGAAGCCCT | 15 | 39 |
| 366798 | 4 | 2509 | CTTGGCTTCTAGAGGAAGCC | 10 | 40 |
| 366799 | 4 | 2529 | CTATAAAAGCACCCCTTTCC | 0 | 41 |
| 366800 | 4 | 2538 | AGCTAGCCTCTATAAAAGCA | 34 | 42 |
| 366801 | 4 | 2547 | AAAAGCAGAAGCTAGCCTCT | 67 | 43 |
| 366802 | 4 | 2554 | AGGGCAGAAAAGCAGAAGCT | 17 | 44 |
| 366803 | 4 | 2595 | AGGCACCATGTCACAGGGTC | 85 | 45 |
| 366804 | 4 | 2606 | GCCTGCCTCTCAGGCACCAT | 51 | 46 |
| 366805 | 4 | 2627 | GGCTGGCGGAGAAGCCTCTA | 49 | 47 |

TABLE 3-continued

Inhibition of human LMNA mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 366806 | 4 | 2647 | TGAGCCTGCCGTCCAGAGGA | 40 | 48 |
| 366807 | 4 | 2727 | ATCACAGCAGGCCAAGCCCA | 33 | 49 |
| 366808 | 4 | 2741 | CCAGGTGTAGTGGAATCACA | 73 | 50 |
| 366809 | 4 | 2821 | TGGTACCTGGGAGAATGGAC | 43 | 51 |
| 366810 | 4 | 2822 | CTGGTACCTGGGAGAATGGA | 38 | 52 |
| 366811 | 4 | 2824 | AGCTGGTACCTGGGAGAATG | 36 | 53 |
| 366812 | 4 | 2835 | AAAGCAAGCGCAGCTGGTAC | 81 | 54 |
| 366813 | 4 | 2840 | ACAGAAAAGCAAGCGCAGCT | 84 | 55 |
| 366814 | 4 | 2857 | TCTTGTCTAAATAAAATACA | 12 | 56 |
| 366815 | 4 | 2860 | ATCTCTTGTCTAAATAAAAT | 0 | 57 |
| 366816 | 4 | 2912 | GCAGCTCAAACTCACCTTTC | 80 | 58 |
| 366817 | 4 | 2917 | GGAAGGCAGCTCAAACTCAC | 69 | 59 |
| 366818 | 4 | 2921 | CTAGGGAAGGCAGCTCAAAC | 69 | 60 |
| 366819 | 4 | 2943 | AGAGCCCACCCAGGGTCTAA | 38 | 61 |
| 366820 | 4 | 2955 | CAGTGACTGCACAGAGCCCA | 70 | 62 |
| 366821 | 4 | 3162 | AGAAACAACTAGTGTATTGA | 68 | 63 |
| 366822 | 6 | 2012 | TCTGGGCTCCTGAGCCGCTG | 26 | 64 |
| 366823 | 6 | 2015 | GGCTCTGGGCTCCTGAGCCG | 16 | 65 |
| 366824 | 6 | 2020 | CTGGGGGCTCTGGGCTCCTG | 22 | 66 |
| 366825 | 6 | 2022 | TTCTGGGGGCTCTGGGCTCC | 25 | 67 |
| 366826 | 6 | 2023 | GTTCTGGGGGCTCTGGGCTC | 27 | 68 |
| 366827 | 6 | 2027 | TGCAGTTCTGGGGGCTCTGG | 43 | 69 |
| 366828 | 6 | 2031 | ATGCTGCAGTTCTGGGGGCT | 17 | 70 |
| 366829 | 7 | 23651 | ATGGCATCAGAAAGTTCCCA | 59 | 71 |
| 366830 | 7 | 23662 | AGGAATATTCCATGGCATCA | 50 | 72 |
| 366831 | 7 | 23668 | TCCCACAGGAATATTCCATG | 63 | 73 |
| 366832 | 7 | 23772 | GATATGCATGCAACAAGAAT | 0 | 74 |
| 366833 | 7 | 23875 | GGAGCAAGCTTGTAGGGCAG | 16 | 75 |
| 366834 | 7 | 23907 | CTCTGAGCTTAAGAGGAAAA | 22 | 76 |
| 366835 | 7 | 24067 | AGGCAGGAAGGTGTGGTTCT | 42 | 77 |
| 366836 | 7 | 24158 | GAAGGGAGACAAGGCTCAGG | 38 | 78 |
| 366837 | 7 | 24461 | GATTTGGAGACAAAGCAGAG | 43 | 79 |
| 366838 | 7 | 24463 | AGGATTTGGAGACAAAGCAG | 41 | 80 |
| 366839 | 7 | 24465 | GCAGGATTTGGAGACAAAGC | 50 | 81 |
| 366840 | 7 | 24466 | TGCAGGATTTGGAGACAAAG | 50 | 82 |
| 366841 | 7 | 24472 | CCCGCCTGCAGGATTTGGAG | 47 | 83 |

TABLE 3-continued

Inhibition of human LMNA mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 366842 | 7 | 24480 | ACCAGGGACCCGCCTGCAGG | 40 | 84 |
| 366843 | 7 | 24489 | CCCTCGATGACCAGGGACCC | 48 | 85 |
| 366844 | 7 | 24491 | ACCCCTCGATGACCAGGGAC | 43 | 86 |
| 366845 | 7 | 24496 | GTCCTACCCCTCGATGACCA | 38 | 87 |
| 366846 | 7 | 24539 | CTGCGGAAGAGAAGGCAGGC | 31 | 88 |

EXAMPLE 4

Antisense Inhibition of Human LMNA by Oligomeric Compounds

A second series of oligomeric compounds was designed to target different regions of human LMNA, using published sequences cited in Table 1. The compounds are shown in Table 4. All compounds in Table 4 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were screened for their modulatory effect on LMNA mRNA levels by quantitative real-time PCR as described in other examples herein. Data are averages from experiments in which T24 cells were treated with the antisense compounds at a concentration of 100 nM. Data are expressed as percent inhibition relative to control-treated cells.

TABLE 4

Inhibition of human LMNA mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 174126 | 4 | 803 | GTTCCTCCTTCATGGTCTGC | 93 | 89 |
| 174127 | 4 | 734 | TCTTGGCCTCACCTAGGGCT | 82 | 90 |
| 174128 | 4 | 1671 | TGCCCAGCCTTCAGGGTGAA | 61 | 91 |
| 174129 | 4 | 1483 | GAAGCTGCTGCGGCTCTCAG | 75 | 92 |
| 174130 | 4 | 1844 | CAACCACAGTCACTGAGCGC | 76 | 93 |
| 174131 | 4 | 370 | CAGCCCTGCGTTCTCCGTTT | 81 | 94 |
| 174132 | 4 | 1410 | GAGTGAGAGGAAGCACGGCC | 51 | 95 |
| 174133 | 4 | 828 | CTGTAGATGTTCTTCTGGAA | 63 | 96 |
| 174134 | 4 | 365 | CTGCGTTCTCCGTTTCCAGC | 85 | 97 |
| 174135 | 4 | 1206 | AGCAGCCGCCGGCTGGTGTC | 56 | 98 |
| 174136 | 4 | 1649 | TTGGTGGGAACCGGTAAGTC | 60 | 99 |
| 174137 | 4 | 1037 | TGTTCCTCTCAGCAGACTGC | 86 | 100 |
| 174138 | 4 | 1637 | GGTAAGTCAGCAAGGGATCA | 75 | 101 |
| 174139 | 4 | 1648 | TGGTGGGAACCGGTAAGTCA | 59 | 102 |
| 174140 | 4 | 844 | CTCACGCAGCTCCTCACTGT | 73 | 103 |
| 174141 | 4 | 1759 | GCAGCCCCAGGTGTTCTGTG | 60 | 104 |
| 174142 | 4 | 121 | GAGACTGCTCGGAGTCGGAG | 55 | 105 |
| 174143 | 4 | 791 | TGGTCTGCAGCCTGTTCTCA | 93 | 106 |

TABLE 4-continued

Inhibition of human LMNA mRNA levels by chimeric oligonucleotides having 2'-MOE wings and deoxy gap

| ISIS # | Target SEQ ID NO | Target Site | Sequence (5' to 3') | % Inhibition | SEQ ID NO |
|---|---|---|---|---|---|
| 174144 | 4 | 1475 | TGCGGCTCTCAGTGGACTCC | 85 | 107 |
| 174145 | 4 | 1040 | TGCTGTTCCTCTCAGCAGAC | 61 | 108 |
| 174146 | 4 | 851 | GCTTGGTCTCACGCAGCTCC | 85 | 109 |
| 174147 | 4 | 1884 | TGATGGAGCAGGTCATCTCC | 29 | 110 |
| 174148 | 4 | 1782 | AGAGCCGTACGCAGGCTGTT | 49 | 111 |
| 174149 | 4 | 376 | AAGGCGCAGCCCTGCGTTCT | 55 | 112 |
| 174150 | 4 | 1170 | GAGTCCTCCAGGTCTCGAAG | 60 | 113 |
| 174151 | 4 | 572 | GGTCACCCTCCTTCTTGGTA | 75 | 114 |
| 174152 | 4 | 257 | ACAGCGGAGTGGAGCTGGCC | 68 | 115 |
| 174153 | 4 | 1597 | CTGCCAATTGCCCATGGACT | 6 | 116 |
| 174154 | 4 | 1129 | CTGCTTCTGGAGCTGGCTGA | 17 | 117 |
| 174155 | 4 | 549 | CGCGCTTTCAGCTCCTTAAA | 86 | 118 |
| 174156 | 4 | 748 | ATCCTGAAGTTGCTTCTTGG | 75 | 119 |
| 174157 | 4 | 465 | GTCTTGCGGGCATCCCCGAG | 64 | 120 |
| 174158 | 4 | 385 | GGTGATGCGAAGGCGCAGCC | 71 | 121 |
| 174159 | 4 | 1491 | TGCTGTGAGAAGCTGCTGCG | 77 | 122 |
| 174160 | 4 | 1428 | CCACCCTGTGTCTGGGATGA | 82 | 123 |
| 174161 | 4 | 1645 | TGGGAACCGGTAAGTCAGCA | 64 | 124 |
| 174162 | 4 | 442 | GGCCTCGTAGGCGGCCTTGA | 54 | 125 |

EXAMPLE 5

Dose-Dependent Inhibition of Human LMNA by Oligomeric Compounds

To further evaluate LMNA antisense compounds, ISIS 174134, ISIS 174137, ISIS 174146, ISIS 366812, ISIS 366813 and ISIS 366816 and a control oligonucleotide were tested in A549 cells at doses of 0.4, 1.2, 3.7, 11, 33 and 100 nM. The compounds were analyzed for their effect on LMNA mRNA levels by quantitative real-time PCR as described in other examples herein.

Table 5 shows the reduction in expression at each dose, expressed as percent inhibition relative to untreated control. If the target expression level of oligomeric compound-treated cell was higher than control, percent inhibition is expressed as zero inhibition.

TABLE 5

Dose-dependent inhibition of LMNA

| ISIS # | 0.4 nM | 1.2 nM | 3.7 nM | 11 nM | 33 nM | 100 nM |
|---|---|---|---|---|---|---|
| 174134 | 0 | 16 | 32 | 43 | 59 | 62 |
| 174137 | 0 | 0 | 0 | 0 | 42 | 48 |
| 174146 | 0 | 5 | 25 | 38 | 62 | 65 |
| 366812 | 0 | 0 | 0 | 17 | 49 | 75 |
| 366813 | 6 | 0 | 17 | 32 | 37 | 71 |
| 366816 | 0 | 0 | 4 | 38 | 58 | 70 |
| Control | 4 | 0 | 8 | 14 | 0 | 0 |

Each of the LMNA antisense compounds demonstrated a dose-dependent inhibition of LMNA mRNA expression.

EXAMPLE 6

Modified LMNA Oligomeric Compounds for Modulation of Splicing

Hutchinson-Gilford progeria syndrome is caused by spontaneous point mutations in LMNA, the most commonly reported of which is a GGC to GGT change at codon 608. This mutation resides in exon 11 of LMNA and results in activation of a cryptic splice site four nucleotides upstream. When the aberrant splice donor site is spliced to the normal exon 12 acceptor site, a truncated LMNA mRNA is produced which lacks 150 nucleotides of exon 11. The truncated mRNA produces a truncated protein lacking 50 amino acids in the globular tail domain. The truncated protein accumulates as farnesyl-prelamin A and cannot be processed to the mature form of the protein, which results in toxicity to the cell and HGPS disease phenotypes.

To modulate splicing of mutant LMNA pre-mRNA, a series of antisense compounds was designed to block the aberrant splice site and promote use of the normal exon 11 splice site. The coding sequence for human LMNA is provided as SEQ ID NO: 4. Exon 11 of normal LMNA includes nucleotides 1911 to 2180 of SEQ ID NO: 4, while the truncated form of LMNA found in HGPS patients ends at nucleotide 2130. Each of the compounds, shown in Table 6, is uniformly modified with 2'-O-(2-methoxyethyl) nucleotides at each position. The internucleoside (backbone) linkages are phosphorothioate throughout the oligonucleotide. All cytidine residues are 5-methylcytidines. The compounds vary in length from 16 to 20 nucleotides. ISIS 355076 and ISIS 355077 were designed to contain a single mismatch relative to the target sequence (SEQ ID NO: 4) in order to be 100% complementary to LMNA sequences containing one of two mutations associated with HGPS (GGC to GGT or GGC to AGC at codon 608).

TABLE 6

Modified LMNA oligomeric compounds for modulation of splicing

| ISIS # | Target SEQ ID NO | Target Site | Sequence (5' to 3') | SEQ ID NO |
|---|---|---|---|---|
| 355067 | 4 | 2021 | GTCCGCCCACCTGGGCTCCT | 126 |
| 355068 | 4 | 2012 | CCTGGGCTCCTGAGCCGCTG | 127 |
| 355069 | 4 | 2001 | GAGCCGCTGGCAGATGCCTT | 128 |
| 355070 | 4 | 1991 | CAGATGCCTTGTCGGCAGGC | 129 |
| 355071 | 4 | 2024 | TGGGTCCGCCCACCTGGGCT | 130 |
| 355072 | 4 | 2035 | CCAGAGGAGATGGGTCCGC | 131 |
| 355073 | 4 | 2048 | TGGAGGCAGAAGAGCCAGAG | 132 |
| 355074 | 4 | 2064 | AGTGACCGTGACACTGGA | 133 |
| 355075 | 4 | 2026 | GGTCCGCCCACCTGGG | 134 |
| 355076 | 4 | 2026 | GGTCCACCCACCTGGG | 135 |
| 355077 | 4 | 2026 | GGTCCGCTCACCTGGG | 136 |

The compounds were analyzed for their effect on LMNA mRNA levels in fibroblast cell lines obtained from four different HGPS patients (Coriell Cell Repository, Camden, N.J.). Two of the cell lines (AG01972 and AG03513E) are derived from patients known to contain the GGC to GGT change at codon 608. The other two cell lines (AG11513A and AG06917B) are derived from HGPS patients with an unknown mutation. A fibroblast cell line derived from a normal parent (AG06299B) was used as a control cell line. Fibroblasts were treated with 200 nM of oligonucleotide for 24 hours. LMNA splice products were analyzed by RT-PCR using primers flanking exon 11 and subjected to electrophoresis using methods well known in the art.

In HGPS patient cell lines treated with uniformly modified antisense compounds, several different effects were observed. In at least one patient cell line, ISIS 355069 and ISIS 355070 appeared to increase the ratio of normal LMNA mRNA to truncated mRNA. However, treatment with ISIS 355074 resulted in a significant increase in truncated LMNA mRNA in both HGPS cell lines and in the normal cell line. This result suggests that ISIS 355074 may target a splice enhancer element required for efficient splicing of the natural LMNA product. Thus, ISIS 355074 effectively inhibited the use of the natural splice site resulting in an increase in use of the cryptic splice site, even in normal cells.

EXAMPLE 7

Identification of Splicing Enhancer Elements and Splicing Silencer Elements using Modified Antisense Compounds: Modulation of LMNA Splicing Products Cis-acting regulatory enhancer and silencer elements, found in exons and introns, play an important role in directing splicing of eukaryotic mRNAs. Exonic splicing enhancer elements, for example, are known to serve as binding sites for SR proteins, which promote splicing by recruiting spliceosomal components. Consensus binding sequences for several SR proteins have been determined (Cartegni et al. 2003, *Nucleic Acids Res.* 31(13):3568-3571). Less is known about trans factors that bind intronic splicing elements, but studies have suggested SR proteins and heterogeneous nuclear ribonucleoproteins (hnRNPs) may play a role in regulating splicing through interaction with intronic elements (Yeo et al. 2004, *Proc. Natl. Acad. Sci. U.S.A.* 101(44):15700-15705). Identification of both intronic and exonic splicing elements is useful for developing therapeutic tools to modulate the splicing process.

Sequence analysis of the binding site for ISIS 355074 reveals a consensus binding sequence (TGTCACG) for the SR protein SRp40 (Cartegni et al. 2003, *Nucleic Acids Res.* 31(13):3568-3571) at nucleotides 2069-2075 of SEQ ID NO: 4. A second SRp40 consensus site (TCACTCG) is also present one nucleotide downstream (3') of the first (nucleotides 2077-2083 of SEQ ID NO: 4), a portion of which is contained within the ISIS 355074 binding site. The SRp40 binding sites are upstream of the normal LMNA splice donor site, indicating they play a role in promoting use of the normal splice site, resulting in production of normal LMNA mRNA. This finding, in combination with the results shown in Example 6, suggest that blocking a SRp40 site(s) with modified antisense compounds such as ISIS 355074 can block binding of SRp40, thus promoting use of the cryptic splice site and generating truncated LMNA mRNA. To further evaluate the effect of modified compounds targeting this region of LMNA, a set of antisense compounds was designed as a micro-walk around the ISIS 335074 binding site. The micro-walk compounds target an exonic region up to about 150 nucleotides upstream (5') of the normal LMNA splice donor site. The sequence and target site (the 5'-most nucleotide of the target nucleic acid to which the compound binds) of the micro-walk compounds are shown in Table 7. Each of the compounds is 18 nucleobases in length and is uniformly modified with 2'-O-(2-methoxyethyl) nucleotides at each position. The internucleoside (backbone) linkages are phosphorothioate throughout the oligonucleotide. All cytidine residues are 5-methylcytidines. Bold residues indicate those that overlap with ISIS 355074.

TABLE 7

Modified compounds designed for ISIS 355074 micro-walk

| ISIS # | Target SEQ ID NO | Target Site | Sequence (5' to 3') | SEQ ID NO |
|---|---|---|---|---|
| 385317 | 4 | 2053 | CACTGGAGGCAGAAGAGC | 137 |
| 385318 | 4 | 2055 | GACACTGGAGGCAGAAGA | 138 |
| 385319 | 4 | 2057 | GTGACACTGGAGGCAGAA | 139 |
| 385320 | 4 | 2059 | CCGTGACACTGGAGGCAG | 140 |
| 385321 | 4 | 2061 | GACCGTGACACTGGAGGC | 141 |
| 355074 | 4 | 2064 | AGTGACCGTGACACTGGA | 133 |
| 385322 | 4 | 2065 | GAGTGACCGTGACACTGG | 142 |
| 385323 | 4 | 2067 | GCGAGTGACCGTGACACT | 143 |
| 385324 | 4 | 2069 | CTGCGAGTGACCGTGACA | 144 |
| 385325 | 4 | 2071 | AGCTGCGAGTGACCGTGA | 145 |
| 385326 | 4 | 2073 | GTAGCTGCGAGTGACCGT | 146 |
| 385327 | 4 | 2075 | CGGTAGCTGCGAGTGACC | 147 |
| 385328 | 4 | 2077 | TGCGGTAGCTGCGAGTGA | 148 |
| 385329 | 4 | 2079 | ACTGCGGTAGCTGCGAGT | 149 |
| 385330 | 4 | 2081 | ACACTGCGGTAGCTGCGA | 150 |
| 385331 | 4 | 2083 | CCACACTGCGGTAGCTGC | 151 |

Shown in Table 8 is the target sequence (SEQ ID NO: 4) for each micro-walk compound. Residues comprising the first SRp40 consensus sequence (TGTCACG) are shown in bold and residues comprising the second SRp40 consensus sequence (TCACTCG) are underlined.

TABLE 8

Target sequences of ISIS 355074 micro-walk compounds

| ISIS # | Target Sequence (5' to 3') | Target nucleotides (SEQ ID NO: 4) | SEQ ID NO |
|---|---|---|---|
| 385317 | GCTCTTCTGCCTCCAGTG | 2053-2070 | 162 |
| 385318 | TCTTCTGCCTCCAGTGTC | 2055-2072 | 163 |
| 385319 | TTCTGCCTCCAGTGTCAC | 2057-2074 | 164 |
| 385320 | CTGCCTCCAGTGTCACGG | 2059-2076 | 165 |
| 385321 | GCCTCCAGTGTCACGGTC | 2061-2078 | 166 |
| 355074 | TCCAGTGTCACGGTCACT | 2064-2081 | 167 |
| 385322 | CCAGTGTCACGGTCACTC | 2065-2082 | 168 |
| 385323 | AGTGTCACGGTCACTCGC | 2067-2084 | 169 |
| 385324 | TGTCACGGTCACTCGCAG | 2069-2086 | 170 |
| 385325 | TCACGGTCACTCGCAGCT | 2071-2088 | 171 |
| 385326 | ACGGTCACTCGCAGCTAC | 2073-2090 | 172 |
| 385327 | GGTCACTCGCAGCTACCG | 2075-2092 | 173 |
| 385328 | TCACTCGCAGCTACCGCA | 2077-2094 | 174 |
| 385329 | ACTCGCAGCTACCGCAGT | 2079-2096 | 175 |
| 385330 | TCGCAGCTACCGCAGTGT | 2081-2098 | 176 |
| 385331 | GCAGCTACCGCAGTGTGG | 2083-3000 | 177 |

The compounds were evaluated for their effect on LMNA splicing in normal fibroblasts. Cells were transfected with 200 nM of each compound shown in Table 7 and RNA was isolated after 24 h. RT-PCR was performed using primers flanking LMNA exon 11 and the products were subjected to electrophoresis using methods well known in the art. In untreated cells or cells treated with a control oligonucleotide, only the normal LMNA mRNA product was detected, as expected. Treatment with the remainder of the LMNA compounds resulted in a mixture of the normal (long form) and truncated (short form) of LMNA mRNA. ISIS 385321, ISIS 385322, ISIS 385323, ISIS 385324, ISIS 385325, ISIS 385326, ISIS 385327, ISIS 385328 and ISIS 355074 promoted production of the truncated form LMNA most effectively. In particular, little to no normal LMNA mRNA was detected following treatment with ISIS 355074, ISIS 385324 or ISIS 385325. The compounds most effective at promoting the short form of LMNA mRNA appeared to be those that completely bound one SRp40 consensus site and at least a portion of the other SRp40 consensus site. ISIS 385324 is completely complementary to both of the consensus sites, ISIS 385325 binds the second consensus site and 5 of 7 nucleotides of the first consensus site while ISIS 355074 binds the first consensus site and 5 of 7 nucleotides of the second site. These results demonstrate that antisense compounds that target a splicing enhancer element for the normal LMNA splice site are capable of modulating the ratio of LMNA splice products to favor the truncated form of LMNA by promoting usage of the cryptic splice site.

To determine whether the LMNA compounds targeting SRp40 consensus sites actually inhibit binding of SRp40 to LMNA mRNA, an ELISA was performed using standard procedures. Normal fibroblasts were either untreated or treated with 10 μM ISIS 385331, ISIS 385324, ISIS 385325 or ISIS 355074 for 48 h. Cell extracts were prepared and incubated with an SRp40 consensus sequence. Binding of SRp40 to LMNA mRNA in the cell extracts was evaluated by ELISA. The results are shown in Table 9 as percent SRp40 binding relative to untreated control.

TABLE 9

Detection of SRp40 binding in cell extracts treated with LMNA compounds

| Treatment | % SRp40 Binding |
|---|---|
| Untreated | 100 |
| ISIS 385331 | 80 |
| ISIS 385324 | 67 |
| ISIS 385325 | 46 |
| ISIS 355074 | 77 |

The results of the SRp40 binding assay are in accordance with the levels of the long and short forms LMNA mRNA observed, suggesting that the modified LMNA antisense compounds alter splicing by inhibiting binding of SRp40.

Next, to determine whether modified compounds could also be designed to promote production of normal LMNA mRNA by targeting (and thus blocking) splicing enhancers for the cryptic splice donor site, a series of compounds was designed to target the region upstream of the cryptic splice site (nucleotides 2030-2036 of SEQ ID NO: 4), which is activated in progeria patients. The compounds target an exonic region up to about 150 nucleotides upstream (5') of the cryptic splice donor site. Each of the compounds, shown in Table 10, is 20 nucleobases in length and is uniformly modified with 2'-O-(2-methoxyethyl) nucleotides at each position. The internucleoside (backbone) linkages are phosphorothioate throughout the oligonucleotide. All cytidine residues are 5-methylcytidines.

TABLE 10

Modified LMNA compounds targeting the region upstream of the LMNA mRNA exon 11 cryptic splice acceptor site

| ISIS # | Target SEQ ID NO | Target Site | Sequence (5' to 3') | SEQ ID NO |
|---|---|---|---|---|
| 386358 | 4 | 1906 | GCTGCAGTGGGAGCCGTGGT | 152 |
| 386359 | 4 | 1908 | CTGCTGCAGTGGGAGCCGTG | 153 |
| 386360 | 4 | 1911 | GAGCTGCTGCAGTGGGAGCC | 154 |
| 386361 | 4 | 1916 | CCCCCGAGCTGCTGCAGTGG | 155 |
| 386362 | 4 | 1920 | GGGTCCCCCGAGCTGCTGCA | 156 |
| 386363 | 4 | 1931 | TGTACTCAGCGGGGTCCCCC | 157 |
| 386364 | 4 | 1938 | CGCAGGTTGTACTCAGCGGG | 158 |
| 386365 | 4 | 1971 | TGCCCGCAGGTCCCGCACAG | 159 |
| 386366 | 4 | 1976 | CAGGCTGCCCGCAGGTCCCG | 160 |
| 386367 | 4 | 1981 | GTCGGCAGGCTGCCCGCAGG | 161 |

The compounds were evaluated for their effect on LMNA splicing in progeria fibroblasts. Cells were transfected with 200 nM of each compound shown in Table 10. Untreated cells and cells treated with a control oligonucleotide or ISIS 355074 were included as controls. RNA was isolated after 24 h. RT-PCR was performed using primers flanking LMNA exon 11 and the products were subjected to electrophoresis using methods well known in the art. In untreated cells and cells treated with a control oligonucleotide, a mixture of the long and short form of LMNA mRNA was observed, as expected for progeria fibroblasts. Supporting the results shown above, treatment with ISIS 355074 resulted in production of only the short form of LMNA mRNA. Treatment with ISIS 386357, ISIS 386358, ISIS 386359, ISIS 386360, ISIS 386361, ISIS 386362, ISIS 386363 and ISIS 386364 resulted in little to minor changes in the ratio of long form to short form of LMNA mRNA and fibroblasts treated with ISIS 386367 appeared to show a modest increase in levels of the long form of LMNA mRNA. In contrast, treatment with ISIS 386365 or ISIS 386366 resulted in a significant shift toward production of the long form of LMNA mRNA. These results demonstrate that ISIS 386365 and ISIS 386366 modulated the ratio of splicing products to favor the normal form by promoting usage of the normal splice donor site.

Sequence analysis of the region upstream of the LMNA cryptic splice site reveals an SC35 consensus binding site (GACCTGCG) at nucleotides 1979-1986 of SEQ ID NO: 4. Shown in Table 11 is the target sequence (SEQ ID NO: 4) for each compound listed in Table 10. Residues comprising the SC35 consensus sequence are shown in bold.

TABLE 11

Target sequences of compounds targeting the region upstream of the cryptic splice site

| ISIS # | Target Sequence (5' to 3') | Target nucleotides (SEQ ID NO: 4) | SEQ ID NO |
|---|---|---|---|
| 386358 | ACCACGGCTCCCACTGCAGC | 1906-1925 | 178 |
| 386359 | CACGGCTCCCACTGCAGCAG | 1908-1927 | 179 |
| 386360 | GGCTCCCACTGCAGCAGCTC | 1911-1930 | 180 |
| 386361 | CCACTGCAGCAGCTCGGGGG | 1916-1935 | 181 |
| 386362 | TGCAGCAGCTCGGGGGACCC | 1920-1939 | 182 |
| 386363 | GGGGGACCCCGCTGAGTACA | 1931-1950 | 183 |
| 386364 | CCCGCTGAGTACAACCTGCG | 1938-1957 | 184 |
| 386365 | CTGTGCGGGACCTGCGGGCA | 1971-1990 | 185 |
| 386366 | CGGGACCTGCGGGCAGCCTG | 1976-1995 | 186 |
| 386367 | CCTGCGGGCAGCCTGCCGAC | 1981-2000 | 187 |

Both ISIS 386365 and ISIS 386366, which were the most effective compounds at altering splicing toward production of the long form of LMNA mRNA, target a region that encompasses the SC35 consensus sequence. Furthermore, ISIS 386367, which also increased the level of normal LMNA mRNA, is complementary to 6 of the 8 nucleotides of the SC35 consensus sequence. These findings suggest that modified compounds targeting the SC35 consensus sequence inhibit use of the cryptic splice site, driving splicing toward production of the long form of LMNA mRNA by promoting usage of the normal splice site. These results also indicate that modified oligonucleotides can be effectively and efficiently used to identify splicing elements such as splicing enhancer elements and splicing silencer elements.

Previous studies have shown that tissue inhibitor of metalloproteinase 3 (TIMP3) is downregulated in fibroblasts of patients diagnosed with progeria (Csoka et al. 2004, *Aging Cell* 3:235-243) and that correction of LMNA aberrant splicing in these cells restores normal expression levels of TIMP3 (Scaffidi and Misteli, 2005, *Nature Med.* 11(4):440-445). To further evaluate the phenotypic effect of the modified LMNA compounds, progeria fibroblasts were treated with selected compounds and expression levels of TIMP3 were determined by RT-PCR using standard procedures. Progeria fibroblasts were either untreated or treated with 180 nM of ISIS 386365, ISIS 386366 or ISIS 386358 for 72 h. Untreated normal fibroblasts were used as a control. Expression levels of TIMP3 are shown in Table 12 as percent mRNA expression relative to untreated progeria fibroblasts.

TABLE 12

Effect of LMNA antisense compounds on TIMP3 expression in progeria fibroblasts

| Fibroblasts | Treatment | % TIMP3 expression |
|---|---|---|
| Normal | Untreated | 343 |
| Progeria | Untreated | 100 |
| Progeria | ISIS 386365 | 204 |
| Progeria | ISIS 386366 | 340 |
| Progeria | ISIS 386358 | 141 |

As previously reported, the level of TIMP3 expression was significantly reduced in untreated progeria fibroblasts relative to untreated normal fibroblasts. ISIS 386258, which had little to no effect on modulating the ratio of LMNA splicing products, led to a slight increase in the level of TIMP3 expression in progeria fibroblasts. However, treatment with ISIS 386365 and ISIS 386366, which significantly promoted splicing of the long form of LMNA mRNA, significantly increased the level of TIMP3 expression in progeria fibroblasts, with ISIS 386366 essentially restoring TIMP3 expression to a normal level. These results demonstrate that modified compounds targeting a splicing enhancer element for the cryptic splice site found in progeria patients can effectively promote splicing of the normal LMNA mRNA and restore normal cellular phenotype.

What is claimed is:

1. A method of modulating splicing of a LMNA pre-mRNA in a cell, comprising contacting the cell with a single-stranded antisense oligomeric compound comprising an oligonucleotide consisting of 12 to 30 linked nucleosides, wherein the oligonucleotide has a nucleobase sequence comprising an at least 8 nucleobase portion complementary to an equal length portion of nucleotides 1983-2062 of SEQ ID NO: 4 and is at least 90% complementary to LMNA pre-mRNA having SEQ ID NO:4 as measured over the entirety of the oligonucleotide, wherein the oligonucleotide comprises at least one modified sugar moiety; and thereby modulating splicing of the LMNA pre-mRNA in the cell, wherein the modulation of splicing results in an increase in the ratio of full-length LMNA mRNA to truncated LMNA mRNA.

2. The method of claim 1, wherein the modulation of splicing results in an increase in the ratio of full-length lamin A protein to truncated lamin A protein.

3. The method of claim 1, wherein the modified sugar moiety is a bicyclic nucleic acid selected from the group consisting of 4'-CH$_2$—O-2' BNA or 4'-CH$_2$CH$_2$—O-2' BNA.

4. The method of claim 3, wherein the modified sugar moiety is a 4'-CH$_2$—O-2' BNA.

5. The method of claim 1, wherein the modified sugar moiety is a 2'-O-(methoxyethyl) modified sugar moiety.

6. The method of claim 1, wherein the cell is in an animal.

7. The method of claim 1, wherein the animal is a human.

8. The method of claim 1, wherein at least one internucleoside linkage of said oligonucleotide is a modified internucleoside linkage.

9. The method of claim 1, wherein each internucleoside linkage of said oligonucleotide is a phosphorothioate internucleoside linkage.

10. The method of claim 1, wherein at least one nucleoside of said oligonucleotide comprises a modified nucleobase.

11. The method of claim 10, wherein the modified nucleobase is a 5-methylcytosine.

12. The method of claim 1, wherein each cytosine in said oligonucleotide is a 5-methylcytosine.

13. The method of claim 1, wherein each nucleoside of the oligonucleotide comprises a 2'-O-(methoxyethyl) modified sugar moiety, wherein each internucleoside linkage of said oligonucleotide is a phosphorothioate internucleoside linkage, and wherein each cytosine in said oligonucleotide is a 5-methylcytosine.

14. The method of claim 1, wherein said oligonucleotide consists of 15 to 30 linked nucleosides.

15. The method of claim 1, wherein said oligonucleotide consists of 18 to 22 linked nucleosides.

16. The method of claim 1, wherein each nucleoside of said oligonucleotide comprises the same modified sugar moiety.

17. The method of claim 16, wherein the modified sugar moiety is a bicyclic nucleic acid selected from the group consisting of 4'-CH$_2$—O-2' BNA or 4'-CH$_2$CH$_2$—O-2' BNA.

18. The method of claim 17, wherein the modified sugar moiety is a 4'-CH$_2$—O-2' BNA.

* * * * *

SEQUENCE LISTING

<160> NUMBER OF SEQ ID NOS: 187

<210> SEQ ID NO 1
<211> LENGTH: 2257
<212> TYPE: DNA
<213> ORGANISM: H. sapiens

<400> SEQUENCE: 1

```
gagcgccgca cctacaccag ccaacccaga tcccgaggtc cgacagcgcc cggcccagat      60
ccccacgcct gccaggagca agccgagagc cagccggccg gcgcactccg actccgagca     120
gtctctgtcc ttcgacccga gccccgcgcc ctttccggga ccctgcccc gcgggcagcg     180
ctgccaacct gccggccatg gagacccgt cccagcggcg cgccacccgc agcggggcgc     240
aggccagctc cactccgctg tcgcccaccc gcatcacccg gctgcaggag aaggaggacc     300
tgcaggagct caatgatcgc ttggcggtct acatcgaccg tgtgcgctcg ctggaaacgg     360
agaacgcagg gctgcgcctt cgcatcaccg agtctgaaga ggtggtcagc cgcgaggtgt     420
ccggcatcaa ggccgcctac gaggccgagc tcggggatgc ccgcaagacc cttgactcag     480
tagccaagga gcgcgcccgc ctgcagctgg agctgagcaa agtgcgtgag gagtttaagg     540
agctgaaagc gcgcaatacc aagaaggagg gtgacctgat agctgctcag gctcggctga     600
aggacctgga ggctctgctg aactccaagg aggccgcact gagcactgct ctcagtgaga     660
agcgcacgct ggagggcgag ctgcatgatc tgcggggcca ggtggccaag cttgaggcag     720
ccctaggtga ggccaagaag caacttcagg atgagatgct gcggcgggtg gatgctgaga     780
acaggctgca gaccatgaag gaggaactgg acttccagaa gaacatctac agtgaggagc     840
tgcgtgagac caagcgccgt catgagaccc gactggtgga gattgacaat gggaagcagc     900
gtgagtttga gagccggctg gcggatgcgc tgcaggaact gcgggcccag catgaggacc     960
aggtggagca gtataagaag gagctggaga agacttattc tgccaagctg gacaatgcca    1020
ggcagtctgc tgagaggaac agcaacctgg tggggctgc ccacgaggag ctgcagcagt    1080
cgcgcatccg catcgacagc ctctctgccc agctcagcca gctccagaag cagctggcag    1140
ccaaggaggc gaagcttcga gacctggagg actcactggc ccgtgagcgg gacaccagcc    1200
ggcggctgct ggcggaaaag gagcgggaga tggccgagat gcgggcaagg atgcagcagc    1260
agctggacga gtaccaggag cttctggaca tcaagctggc cctggacatg gagatccacg    1320
cctaccgcaa gctcttggag ggcgaggagg agaggctacg cctgtccccc agccctacct    1380
cgcagcgcag ccgtggccgt gcttcctctc actcatccca gacacagggt ggggcagcg    1440
tcaccaaaaa gcgcaaactg gagtccactg agagccgcag cagcttctca cagcacgcac    1500
```

| | |
|---|---|
| gcactagcgg gcgcgtggcc gtggaggagg tggatgagga gggcaagttt gtccggctgc | 1560 |
| gcaacaagtc caatgaggac cagtccatgg gcaattggca gatcaagcgc cagaatggag | 1620 |
| atgatccctt gctgacttac cggttcccac caaagttcac cctgaaggct gggcaggtgg | 1680 |
| tgacgatctg ggctgcagga gctggggcca cccacagccc ccctaccgac ctggtgtgga | 1740 |
| aggcacagaa cacctggggc tgcgggaaca gcctgcgtac ggctctcatc aactccactg | 1800 |
| gggaagaagt ggccatgcgc aagctggtgc gctcagtgac tgtggttgag gacgacgagg | 1860 |
| atgaggatgg agatgaccct ctccatcacc accacggctc ccactgcagc agctcggggg | 1920 |
| accccgctga gtacaacctg cgctcgcgca ccgtgctgtg cgggacctgc gggcagcctg | 1980 |
| ccgacaaggc atctgccagc ggctcaggag cccagagccc cagaactgc agcatcatgt | 2040 |
| aatctgggac ctgccaggca ggggtggggg tggaggcttc ctgcgtcctc ctcacctcat | 2100 |
| gcccacccc tgccctgcac gtcatgggag ggggcttgaa gccaaagaaa aataacccctt | 2160 |
| tggttttttt cttctgtatt tttttttcta agagaagtta ttttctacag tggttttata | 2220 |
| ctgaaggaaa aacacaagca aaaaaaaaaa aaaaaaa | 2257 |

<210> SEQ ID NO 2
<211> LENGTH: 2407
<212> TYPE: DNA
<213> ORGANISM: H. sapiens

<400> SEQUENCE: 2

| | |
|---|---|
| gagcgccgca cctacaccag ccaacccaga tcccgaggtc cgacagcgcc cggcccagat | 60 |
| ccccacgcct gccaggagca agccgagagc cagccggccg cgcactccg actccgagca | 120 |
| gtctctgtcc ttcgacccga gccccgcgcc cttttcggga cccctgcccc gcgggcagcg | 180 |
| ctgccaacct gccggccatg gagacccgt cccagcggcg cgccaccgc agcggggcgc | 240 |
| aggccagctc cactccgctg tcgcccaccc gcatcacccg gctgcaggag aaggaggacc | 300 |
| tgcaggagct caatgatcgc ttggcggtct acatcgaccg tgtgcgctcg ctggaaacgg | 360 |
| agaacgcagg gctgcgcctt cgcatcaccg agtctgaaga ggtggtcagc cgcgaggtgt | 420 |
| ccggcatcaa ggccgcctac gaggccgagc tcggggatgc ccgcaagacc cttgactcag | 480 |
| tagccaagga gcgcgcccgc ctgcagctgg agctgagcaa agtgcgtgag gagtttaagg | 540 |
| agctgaaagc gcgcaatacc aagaaggagg gtgacctgat agctgctcag gctcggctga | 600 |
| aggacctgga ggctctgctg aactccaagg aggccgcact gagcactgct ctcagtgaga | 660 |
| agcgcacgct ggagggcgag ctgcatgatc tgcggggcca ggtggccaag cttgaggcag | 720 |
| ccctaggtga ggccaagaag caacttcagg atgagatgct gcggcgggtg gatgctgaga | 780 |
| acaggctgca gaccatgaag gaggaactgg acttccagaa gaacatctac agtgaggagc | 840 |
| tgcgtgagac caagcgccgt catgagaccc gactggtgga gattgacaat gggaagcagc | 900 |
| gtgagtttga gagccggctg gcggatgcgc tgcaggaact gcgggcccag catgaggacc | 960 |
| aggtggagca gtataagaag gagctggaga agacttattc tgccaagctg gacaatgcca | 1020 |
| ggcagtctgc tgagaggaac agcaacctgg tgggggctgc ccacgaggag ctgcagcagt | 1080 |
| cgcgcatccg catcgacagc ctctctgccc agctcagcca gctccagaag cagctggcag | 1140 |
| ccaaggaggc gaagcttcga gacctggagg actcactggc ccgtgagcgg gacaccagcc | 1200 |
| ggcggctgct ggcggaaaag gagcgggaga tggccgagat gcgggcaagg atgcagcagc | 1260 |
| agctggacga gtaccaggag cttctggaca tcaagctggc cctggacatg gagatccacg | 1320 |
| cctaccgcaa gctcttggag ggcgaggagg agaggctacg cctgtccccc agccctacct | 1380 |

-continued

```
cgcagcgcag ccgtggccgt gcttcctctc actcatccca gacacagggt gggggcagcg    1440
tcaccaaaaa gcgcaaactg gagtccactg agagccgcag cagcttctca cagcacgcac    1500
gcactagcgg gcgcgtggcc gtggaggagg tggatgagga gggcaagttt gtccggctgc    1560
gcaacaagtc caatgaggac cagtccatgg caattggca gatcaagcgc cagaatggag     1620
atgatccctt gctgacttac cggttcccac caaagttcac cctgaaggct gggcaggtgg    1680
tgacgatctg ggctgcagga gctggggcca cccacagccc ccctaccgac ctggtgtgga    1740
aggcacagaa cacctggggc tgcgggaaca gcctgcgtac ggctctcatc aactccactg    1800
gggaagaagt ggccatgcgc aagctggtgc gctcagtgac tgtggttgag gacgacgagg    1860
atgaggatgg agatgacctg ctccatcacc accacggctc ccactgcagc agctcggggg    1920
accccgctga gtacaacctg cgctcgcgca ccgtgctgtg cgggacctgc gggcagcctg    1980
ccgacaaggc atctgccagc ggctcaggag cccaggtggg cggacccatc tcctctggct    2040
cttctgcctc cagtgtcacg gtcactcgca gctaccgcag tgtgggggc agtgggggtg     2100 gcagcttcgg ggacaatctg gtcacccgct cctacctcct gggcaactcc agccccgaa    2160 cccagagccc ccagaactgc agcatcatgt aatctgggac ctgccaggca ggggtggggg    2220
tggaggcttc ctgcgtcctc ctcacctcat gcccacccc tgccctgcac gtcatgggag      2280
ggggcttgaa gccaaagaaa aataacccctt tggtttttt cttctgtatt ttttttcta      2340 agagaagtta ttttctacag tggttttata ctgaaggaaa aacacaagca aaaaaaaaa     2400 aaaaaaa                                                                2407
```

<210> SEQ ID NO 3
<211> LENGTH: 2032
<212> TYPE: DNA
<213> ORGANISM: H. sapiens

<400> SEQUENCE: 3

```
actcagtgtt cgcgggagcg ccgcacctac accagccaac ccagatcccg aggtccgaca     60
gcgcccggcc cagatcccca cgcctgccag gagcaagccg agagccagcc ggccggcgca    120
ctccgactcc gagcagtctc tgtccttcga cccgagcccc gcgcccttc cgggaccccct    180 gccccgcggg cagcgctgcc aacctgccgg ccatgccgga cccgtcccag cggcgcgcca    240
cccgcagcgg ggcgcaggcc agctccactc cgctgtcgcc cacccgcatc acccggctgc    300
aggagaagga ggacctgcag gagctcaatg atcgcttggc ggtctacatc gaccgtgtgc    360
gctcgctgga aacggagaac gcagggctgc gccttcgcat caccgagtct gaagaggtgg    420
tcagccgcga ggtgtccggc atcaaggccg cctacgaggc cgagctcggg gatgcccgca    480 agaccccttga ctcagtagcc aaggagcgcg cccgcctgca gctggagctg agcaaagtgc    540
gtgaggagtt taaggagctg aaagcgcgca ataccaagaa ggagggtgac ctgatagctg    600
ctcaggctcg gctgaaggac ctggaggctc tgctgaactc caaggaggcc gcactgagca    660
ctgctctcag tgagaagcgc acgctggagg gcgagctgca tgatctgcgg ggccaggtgg    720
ccaagcttga ggcagcccta ggtgaggcca agaagcaact tcaggatgag atgctgcggc    780
gggtggatgc tgagaacagg ctgcagacca tgaaggagga actggacttc cagaagaaca    840
tctacagtga ggagctgcgt gagaccaagc gccgtcatga gacccgactg gtggagattg    900
acaatgggaa gcagcgtgag tttgagagcc ggctggcgga tgcgctgcag gaactgcggg    960
cccagcatga ggaccaggtg gagcagtata agaaggagct ggagaagact tattctgcca   1020
```

```
agctggacaa tgccaggcag tctgctgaga ggaacagcaa cctggtgggg gctgcccacg    1080
aggagctgca gcagtcgcgc atccgcatcg acagcctctc tgcccagctc agccagctcc    1140
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggccctgg    1320
acatggagat ccacgcctac cgcaagctct tggagggcga ggaggagagg ctacgcctgt    1380
cccccagccc tacctcgcag cgcagccgtg gccgtgcttc ctctcactca tcccagacac    1440
agggtggggg cagcgtcacc aaaaagcgca aactggagtc cactgagagc cgcagcagct    1500
tctcacagca cgcacgcact agcgggcgcg tggccgtgga ggaggtggat gaggagggca    1560
agtttgtccg gctgcgcaac aagtccaatg gaccagtc catgggcaat tggcagatca    1620
agcgccagaa tggagatgat cccttgctga cttaccggtt cccaccaaag ttcaccctga    1680
aggctgggca ggtggtgacg atctgggctg caggagctgg ggccacccac agccccccta    1740
ccgacctggt gtggaaggca cagaacacct ggggctgcgg gaacagcctg cgtacggctc    1800
tcatcaactc cactggggaa gaagtggcca tgcgcaagct ggtgcgctca gtgactgtgg    1860
ttgaggacga cgaggatgag gatggagatg acctgctcca tcaccaccac gtgagtggta    1920
gccgccgctg aggccgagcc tgcactgggg ccacccagcc aggcctgggg gcagcctctc    1980
cccagcctcc ccgtgccaaa aatctttca ttaaagaatg ttttggaact tt    2032

<210> SEQ ID NO 4
<211> LENGTH: 3181
<212> TYPE: DNA
<213> ORGANISM: H. sapiens

<400> SEQUENCE: 4
actcagtgtt cgcgggagcg ccgcacctac accagccaac ccagatcccg aggtccgaca      60
gcgcccggcc cagatcccca cgcctgccag gagcaagccg agagccagcc ggccggcgca     120
ctccgactcc gagcagtctc tgtccttcga cccgagcccc gcgccctttc cgggacccct     180
gccccgcggg cagcgctgcc aacctgccgg ccatggagac cccgtcccag cggcgcgcca     240
cccgcagcgg ggcgcaggcc agctccactc cgctgtcgcc cacccgcatc acccggctgc     300
aggagaagga ggacctgcag gagctcaatg atcgcttggc ggtctacatc gaccgtgtgc     360
gctcgctgga aacggagaac gcagggctgc gccttcgcat caccgagtct gaagaggtgg     420
tcagccgcga ggtgtccggc atcaaggcc cctacgaggc cgagctcggg gatgcccgca     480
agacccttga ctcagtagcc aaggagcgcg cccgcctgca gctggagctg agcaaagtgc     540
gtgaggagtt taaggagctg aaagcgcgca ataccaagaa ggagggtgac ctgatagctg     600
ctcaggctcg gctgaaggac ctggaggctc tgctgaactc caaggaggcc gcactgagca     660
ctgctctcag tgagaagcgc acgctggagg gcgagctgca tgatctgcgg ggccaggtgg     720
ccaagcttga ggcagcccta ggtgaggcca agaagcaact tcaggatgag atgctgcggc     780
gggtggatgc tgagaacagg ctgcagacca tgaaggagga actggacttc agaagaaca     840 tctacagtga ggagctgcgt gagaccaagc gccgtcatga cccgactg gtggagattg     900 acaatgggaa gcagcgtgag tttgagagcc ggctggcgga tgcgctgcag gaactgcggg     960 ccagcatga ggaccaggtg gagcagtata agaaggagct ggagaagact tattctgcca    1020
agctggacaa tgccaggcag tctgctgaga ggaacagcaa cctggtgggg gctgcccacg    1080
aggagctgca gcagtcgcgc atccgcatcg acagcctctc tgcccagctc agccagctcc    1140
```

```
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggccctgg    1320
acatggagat ccacgcctac cgcaagctct tggagggcga ggaggagagg ctacgcctgt    1380
cccccagccc tacctcgcag cgcagccgtg ccgtgcttc ctctcactca tcccagacac    1440
agggtggggg cagcgtcacc aaaaagcgca aactggagtc cactgagagc cgcagcagct    1500
tctcacagca cgcacgcact agcgggcgcg tggccgtgga ggaggtggat gaggagggca    1560
agtttgtccg gctgcgcaac aagtccaatg gaccagtc catgggcaat ggcagatca     1620 agcgccagaa tggagatgat cccttgctga cttaccggtt cccaccaaag ttcaccctga    1680
aggctgggca ggtggtgacg atctgggctg caggagctgg ggccacccac agccccccta    1740
ccgacctggt gtggaaggca cagaacacct ggggctgcgg gaacagcctg cgtacggctc    1800
tcatcaactc cactggggaa gaagtggcca tgcgcaagct ggtgcgctca gtgactgtgg    1860
ttgaggacga cgaggatgag gatggagatg acctgctcca tcaccaccac ggctcccact    1920
gcagcagctc gggggacccc gctgagtaca acctgcgctc gcgcaccgtg ctgtgcggga    1980
cctgcgggca gcctgccgac aaggcatctg ccagcggctc aggagcccag gtgggcggac    2040
ccatctcctc tggctcttct gcctccagtg tcacggtcac tcgcagctac cgcagtgtgg    2100
ggggcagtgg gggtggcagc ttcggggaca atctggtcac ccgctcctac ctcctgggca    2160
actccagccc ccgaacccag agcccccaga actgcagcat catgtaatct gggacctgcc    2220 aggcagggt ggggtggag gcttcctgcg tcctcctcac ctcatgccca cccctgccc     2280 tgcacgtcat gggaggggc ttgaagccaa agaaaaataa ccctttggtt tttttcttct    2340 gtatttttt ttctaagaga agttattttc tacagtggtt ttatactgaa ggaaaaacac    2400
aagcaaaaaa aaaaaaaagc atctatctca tctatctcaa tcctaatttc tcctcccttc    2460
cttttccctg cttccaggaa actccacatc tgccttaaaa ccaagagggg cttcctctag    2520
aagccaaggg aaaggggtgc ttttatagag gctagcttct gcttttctgc cctggctgct    2580
gcccccaccc cggggaccct gtgacatggt gcctgagagg caggcataga ggcttctccg    2640
ccagcctcct ctggacggca ggctcactgc caggccagcc tccgagaggg agagagagag    2700
agagaggaca gcttgagccg ggcccctggg ctttggcctgc tgtgattcca ctacacctgg    2760
ctgaggttcc tctgcctgcc ccgcccccag tcccaccccc tgccccagc cccggggtga    2820 gtccattctc ccaggtacca gctgcgcttg cttttctgta ttttatttag acaagagatg    2880
ggaatgaggt gggaggtgga agaagggaga agaaggtga gtttgagctg ccttccctag    2940
ctttagaccc tgggtgggct ctgtgcagtc actggaggtt gaagccaagt gggtgctgg    3000 gaggagggag agggaggtca ctggaaaggg gagagcctgc tggcacccac cgtggaggag    3060
gaaggcaaga gggggtggag gggtgtggca gtggttttgg caaacgctaa agagcccttg    3120
cctccccatt tccatctgc accccttctc tcctccccaa atcaatacac tagttgtttc    3180
t                                                                   3181
```

<210> SEQ ID NO 5
<211> LENGTH: 3091
<212> TYPE: DNA
<213> ORGANISM: H. sapiens

<400> SEQUENCE: 5

```
actcagtgtt cgcgggagcg ccgcacctac accagccaac ccagatcccg aggtccgaca      60
gcgcccggcc cagatcccca cgcctgccag gagcaagccg agagccagcc ggccggcgca     120
ctccgactcc gagcagtctc tgtccttcga cccgagcccc gcgcccttc  cgggacccct     180 gccccgcggg cagcgctgcc aacctgccgg ccatggagac cccgtcccag cggcgcgcca     240
cccgcagcgg ggcgcaggcc agctccactc cgctgtcgcc cacccgcatc acccggctgc     300
aggagaagga ggacctgcag gagctcaatg atcgcttggc ggtctacatc gaccgtgtgc     360
gctcgctgga aacggagaac gcagggctgc gccttcgcat caccgagtct gaagaggtgg     420
tcagccgcga ggtgtccggc atcaaggccg cctacgaggc cgagctcggg gatgcccgca     480
agaccctgta ctcagtagcc aaggagcgcg cccgcctgca gctggagctg agcaaagtgc     540
gtgaggagtt taaggagctg aaagcgcgca ataccaagaa ggagggtgac ctgatagctg     600
ctcaggctcg gctgaaggac ctggaggctc tgctgaactc caaggaggcc gcactgagca     660
ctgctctcag tgagaagcgc acgctggagg gcgagctgca tgatctgcgg ggccaggtgg     720
ccaagcttga ggcagcccta ggtgaggcca agaagcaact tcaggatgag atgctgcggc     780
gggtggatgc tgagaacagg ctgcagacca tgaaggagga actggacttc cagaagaaca     840
tctacagtga ggagctgcgt gagaccaagc gccgtcatga acccgactg  gtggagattg     900 acaatgggaa gcagcgtgag tttgagagcc ggctggcgga tgcgctgcag gaactgcggg     960
cccagcatga ggaccaggtg gagcagtata agaaggagct ggagaagact tattctgcca    1020
agctggacaa tgccaggcag tctgctgaga ggaacagcaa cctggtgggg gctgcccacg    1080
aggagctgca gcagtcgcgc atccgcatcg acagcctctc tgcccagctc agccagctcc    1140
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggccctgg    1320
acatggagat ccacgcctac cgcaagctct ggaggcgcga ggaggagagg ctacgcctgt    1380
cccccagccc tacctcgcag cgcagccgtg gccgtgcttc ctctcactca tcccagacac    1440
agggtggggg cagcgtcacc aaaaagcgca aactggagtc cactgagagc cgcagcagct    1500
tctcacagca cgcacgcact agcgggcgcg tggccgtgga ggaggtggat gaggagggca    1560
agtttgtccg gctgcgcaac aagtccaatg aggaccagtc catgggcaat tggcagatca    1620
agcgccagaa tggagatgat cccttgctga cttaccggtt cccaccaaag ttcaccctga    1680
aggctgggca ggtggtgacg atctgggctg caggagctgg ggccacccac agcccccta     1740 ccgacctggt gtggaaggca cagaacacct ggggctgcgg gaacagcctg cgtacggctc    1800
tcatcaactc cactggggaa ggctcccact gcagcagctc gggggacccc gctgagtaca    1860
acctgcgctc gcgcaccgtg ctgtgcggga cctgcgggca gctgccgac  aaggcatctg    1920 ccagcggctc aggagcccag gtgggcggac ccatctcctc tggctcttct gcctccagtg    1980
tcacggtcac tcgcagctac cgcagtgtgg ggggcagtgg gggtggcagc ttcggggaca    2040
atctggtcac ccgctcctac ctcctgggca actccagccc ccgaacccag agcccccaga    2100
actgcagcat catgtaatct gggacctgcc aggcagggt  ggggtggag  gcttcctgcg    2160 tcctcctcac ctcatgccca ccccctgccc tgcacgtcat gggagggggc ttgaagccaa    2220
agaaaaataa ccctttggtt ttttcttct  gtattttttt ttctaagaga agttattttc    2280
tacagtggtt ttatactgaa ggaaaaacac aagcaaaaaa aaaaaaaagc atctatctca    2340
tctatctcaa tcctaatttc tcctcccttc cttttccctg cttccaggaa actccacatc    2400
```

| | |
|---|---|
| tgccttaaaa ccaaagaggg cttcctctag aagccaaggg aaaggggtgc ttttatagag | 2460 |
| gctagcttct gcttttctgc cctggctgct gcccccaccc cggggacccct gtgacatggt | 2520 |
| gcctgagagg caggcataga ggcttctccg ccagcctcct ctggacggca ggctcactgc | 2580 |
| caggccagcc tccgagaggg agagagagag agagaggaca gcttgagccg ggcccctggg | 2640 |
| cttggcctgc tgtgattcca ctacacctgg ctgaggttcc tctgcctgcc ccgcccccag | 2700 |
| tccccacccc tgccccagcc cccggggtga gtccattctc ccaggtacca gctgcgcttg | 2760 |
| cttttctgta ttttatttag acaagagatg ggaatgaggt gggaggtgga agaagggaga | 2820 |
| agaaaggtga gtttgagctg ccttccctag ctttagaccc tgggtgggct ctgtgcagtc | 2880 |
| actggaggtt gaagccaagt ggggtgctgg gaggagggag agggaggtca ctggaaaggg | 2940 |
| gagagcctgc tggcacccac cgtggaggag gaaggcaaga gggggtggag gggtgtggca | 3000 |
| gtggttttgg caaacgctaa agagcccttg cctccccatt tcccatctgc accccttctc | 3060 |
| tcctccccaa atcaatacac tagttgtttc t | 3091 |

<210> SEQ ID NO 6
<211> LENGTH: 1749
<212> TYPE: DNA
<213> ORGANISM: H. sapiens

<400> SEQUENCE: 6

| | |
|---|---|
| tctcctcagc tccttcccgc cgcccagtct ggatcctggg ggaggcgctg aagtcggggc | 60 |
| ccgccctgtg gccccgcccg gcccgcgctt gctagcgccc aaagccagcg aagcacgggc | 120 |
| ccaaccgggc catgtcgggg gagcctgagc tcattgagct gcgggagctg gcacccgctg | 180 |
| ggcgcgctgg gaagggccgc acccggctgg agcgtgccaa cgcgctgcgc atcgcgcggg | 240 |
| gcaccgcgtg caaccccaca cggcagctgg tccctggccg tggccaccgc ttccagcccg | 300 |
| cggggcccgc cacgcacacg tggtgcgacc tctgtggcga cttcatctgg ggcgtcgtgc | 360 |
| gcaaaggcct gcagtgcgcg caacaaggac ggttcttaca caggcttcat caaggttcag | 420 |
| ctgaagctgg tgcgccctgt ctctgtgccc tccagcaaga agccaccctc cttgcaggat | 480 |
| gcccggcggg gcccaggacg gggcacaagt gtcaggcgcc gcacttcctt ttacctgccc | 540 |
| aaggatgctg tcaagcacct gcatgtgctg tcacgcacaa gggcacgtga agtcattgag | 600 |
| gccctgctgc gaaagttctt ggtggtggat gaccccccgca gtttgcact ctttgagcgc | 660 |
| gctgagcgtc acggccaagt gtacttgcgg aagctgttgg atgatgagca gcccctgcgg | 720 |
| ctgcggctcc tggcagggcc cagtgacaag gccctgagct ttgtcctgaa ggaaaatgac | 780 |
| tctggggagg tgaactggga cgccttcagc atgcctgaac tacataactt cctacgtatc | 840 |
| ctgcagcggg aggaggagga gcacctccgc cagatcctgc agaagtactc ctattgccgc | 900 |
| cagaagatcc aagaggccct gcacgcctgc ccccttgggt gacctcttgt acccccaggt | 960 |
| ggaaggcaga cagcaggcag cgccaagtgc gtgccgtgtg agtgtgacag gccagtggg | 1020 |
| gcctgtggaa tgagtgtgca tggaggccct cctgtgctgg gggaatgagc ccagagaaca | 1080 |
| gcgaagtagc ttgctccctg tgtccacctg tgggtgtagc caggtatggc tctgcacccc | 1140 |
| tctgccctca ttactgggcc ttagtgggcc agggctgccc tgagaagctg ctccaggcct | 1200 |
| gcagcaggag tggtgcagac agaagtctcc tcaattttg tctcagaagt gaaaatcttg | 1260 |
| gagaccctgc aaacagaaca gggtcatgtt tgcaggggtg acggccctca tctatgagga | 1320 |
| aaggttttgg atcttgaatg tggtctcagg atatccttat cagagctaag ggtgggtgct | 1380 |

| | |
|---|---:|
| cagaataagg caggcattga ggaagagtct tggtttctct ctacagtgcc aactcctcac | 1440 |
| acaccctgag gtcagggagt gctggctcac agtacagcat gtgccttaat gcttcatatg | 1500 |
| aggaggatgt ccctgggcca gggtctgtgt gaatgtgggc actggcccag gttcatacct | 1560 |
| tatttgctaa tcaaagccag ggtctctccc tcaggtgttt tttatgaagt gcgtgaatgt | 1620 |
| atgtaatgtg tggtggcctc agctgaatgc ctcctgtggg gaaaggggtt ggggtgacag | 1680 |
| tcatcatcag ggcctggggc ctgagagaat tggctcaata aagatttcaa gatcctcaaa | 1740 |
| aaaaaaaaa | 1749 |

<210> SEQ ID NO 7
<211> LENGTH: 26174
<212> TYPE: DNA
<213> ORGANISM: H. sapiens

<400> SEQUENCE: 7

| | |
|---|---:|
| agcctcagcc ctcccccac tttcctggct cccagccctg cctacctgac cctctccctt | 60 |
| gctttgcgcc cacttccctc tctttctccc cgacccttt gcccaccac tctccctcct | 120 |
| tggctctgcc ctctagccca gaaggtctga ggcaatgggg gcaagcttgg agccgacagt | 180 |
| gctgagcagg caggagccaa gagaggggaa gcttgagcct cacgcagtta ggggtgcgct | 240 |
| ggagagggtg gggcccgact ccgccacacc ccaacggtcc ttccccctcc tcaccactcc | 300 |
| cgcccccacc cccaatggat ctgggactgc ccctttaaga gtagtggccc ctcctccctt | 360 |
| cagaggagga cctattagag cctttgcccc ggcgtcggtg actcagtgtt cgcgggagcg | 420 |
| ccgcacctac accagccaac ccagatcccg aggtccgaca cgcccggcc cagatcccca | 480 |
| cgcctgccag gagcaagccg agagccagcc ggccggcgca ctccgactcc gagcagtctc | 540 |
| tgtccttcga cccgagcccc gcgcccttc cgggacccct gccccgcggg cagcgctgcc | 600 |
| aacctgccgg ccatggagac cccgtcccag cggcgcgcca cccgcagcgg ggcgcaggcc | 660 |
| agctccactc cgctgtcgcc cacccgcatc acccggctgc aggagaagga ggacctgcag | 720 |
| gagctcaatg atcgcttggc ggtctacatc gaccgtgtgc gctcgctgga aacggagaac | 780 |
| gcagggctgc gccttcgcat caccgagtct gaagaggtgg tcagccgcga ggtgtccggc | 840 |
| atcaaggccg cctacgaggc cgagctcggg gatgcccgca agacccttga ctcagtagcc | 900 |
| aaggagcgcg cccgcctgca gctggagctg agcaaagtgc gtgaggagtt taaggagctg | 960 |
| aaagcgcggt gagttcgccc aggtggctgc gtgcctggcg gggagtggag agggcggcgg | 1020 |
| gccggcgccc ctggccggcc gcaggaaggg agtgagaggg cctggaggcc gataactttg | 1080 |
| ccatagtctc ctccctcccc ggaactgccc ccagcgggtg actggcagtg tcaaggggaa | 1140 |
| ttgtcaagac aggacagaga gggaagtggt ggtctctggg agagggtcgg ggaggatata | 1200 |
| aggaatggtg ggggtatcag ggacaagttg gggctggggc cggcctgaat tcggtcagat | 1260 |
| tgggatttgc caactatttg gagccggggg gagggcttg agcaaaacag aactagccct | 1320 |
| gccagctcga agaactctgg gcacccagga cacatcggag tggcagaaag ggtcctgtta | 1380 |
| gaactttgtt agcgggcttg gcactgtgct agctttgccc aagctggctc tgaacacatg | 1440 |
| atgcccacta agacataact ctcaagttgg catctgtcca gcgtgttgga gcgaggtcag | 1500 |
| gaaggcaggg caatcccct tttccctccc aagggcttgg cggtggcccc ccctcagcat | 1560 |
| gaccttgtcc tgggttctaa gggttgggaa gttctccctc actctgccac tctgcgtgtc | 1620 |
| tgggaccttc cttgggctct gacaggccca ccaaaagagc tccggagat gagagatcgg | 1680 |
| ctccccccgca gctcccacag cccttggcct gcttggccca ggaatgcaag ggagggaggg | 1740 |

```
aggcagaggg cagaggctcc cagctcagga agttgtgtta tgcccaggtc tggccgcact     1800
cctcccttgg ccctctgcct agtgtcttcg agggttgggg gcactgtcct tccctccttg     1860
gggtgagcca ctttcatttt cccagcgggg ccaggcagtc tttgctcggg cccatcctct     1920
tagctgctga cgttttgatc tttgtcttat tgaagtgctg gaatacagtg acattttga      1980 aatccagccg ttggaagatt caggccactc ccactttacc caccectgcc ccaccctacc     2040 ccaccctact caactgcacc ttcttctttt ctaaaaaagc ctttgggagc ttggaagtat     2100
aggccctctc ttccagcccc atcaaaattt gtttccctte ttcctgcctt cccttteter     2160 atgcagaccc aggccaagag cactaagggt gcttggagat ccgtaaaggg ctgttggctt     2220
tgacttcttc tctctcttt atcatctact ccaaacttct gctcttccta gaacccttrg     2280
ctaggtgtgg ttttgttgcc caggctggag tgcaatggca caatctcggc tcactgcaac     2340
ctccgcctcc caggttcaag tgattctcct gcctcagcct cccgaatagc tgagattaca     2400
ggcatgtgcc accatgccgg ctaattttrg tatttctagt agagatgggg tttctccatg     2460
ttcgtcaggc tagtcttgaa ctcccaacct caggtgatcc acccgcctca gcctcccaaa     2520
gtgctaggat tacaggcatg agccaccacg ctgggcccat cacccttctt tctgaagagt     2580
caatggaagt tgtgtgtagg aagacaggct taacggtttt ttttrgagac agggtcttac     2640
tctgtcaccc agactggagt gaagtggtgc gatcttggct caccacaacc tctgcctccc     2700
aggctcaaaa gattctcctg cctcagcctc ctgagtagct gggattataa gtgtgtgcca     2760
ccacacatgg ctattttttt tttttttttt tttttaatt tttagtagag atggggtttc      2820
accatgttgg ctaggctggt ctcaaactcc tgacttcaaa tgatccacct gcctcggcct     2880
cccaaagtgc tgggattaca ggtgtgagct accatgcccg gccatcaacc tttattttgt     2940
tttttrgaga cggagtcttg ctttgttgcc caggctggag tacagtagtg tgacctcagg     3000
tcactgcaac ctctgcctcc caggttcaag ccatgctcct gcctcagcct cccaagtagc     3060
tgggactata ggtgcctgcc accacgcccg gctacttttt atattttag tagagacggg      3120 gtttcaccat gttggccagg gtgatctcga actcctgacc tcaagtgatc tgcctgcctc     3180
agcctcccaa agtgttggga ttagagacgg gagccactgc gcctggcttc ttttttttctt    3240 gagatagggt ttcactctgt tacccaggct ggagtgcagt ggcaaggtca tggctcactg     3300
cagcctctac ctctctggct caagccatcc tcccgcctca gcctcctgag tagctgggac     3360
cacaggcagg caccaccacc cacagctaat gttttgtat tattttgtag atgggggtt       3420 ttgccatgtt gcccacagtc ttgaactcct gggttcattc tgctgaaaga ccacacct       3480 gtccttttct ttattttat tatattttc agagacaggg ccttgccctg ttgctcaggc       3540
tagagtgcaa tggtacaatc ataacttgct gcagcctgga actcctcctg ggctcaagcg     3600
atcctaccgt ctcaccttcc ggaatagctg agactaaggg caggcaccac cacgcttggc     3660 taatttttt ttttttttt tttttttgc ttttgtttg taaagatgga aacttgctat         3720
gttgctcagc tggttccgaa gttttggcct caagcaatcc tcctgcctcg gcctccggaa     3780
gcactgggat tacaggcata agccaccagg cctgacgcca ggcctgtctt ttttctacta     3840
gtgatatgaa caatttagtt agcaagacag ataggaagca aggaagggga gacccagaga     3900
attcgttgca ttctaaacta gtccactcat ctaccaaagc cctgtgaagg acattttrag     3960
cagttttagc agttttctgg tcaaaacttt gatcgagaaa cagattgagt ggattcgata     4020
ttctcttgct cacccagcca cgccagtttg tctcctctgc ctcctagtgc agctgtccag     4080
```

```
gcctgggaca ccaggcgggt atgtgcgcat gtggggcagg gcggaggtgg tgtgtgtact    4140
tgttatattt agccacctcc ctctgttctc ccccactgat cctggctgga aaggctgggc    4200
ttccggaaaa gagaggtgga tttgcacacc tggatcccaa gctgatagaa agtggggtga    4260
agacaaaggg gactcagact ggggtgtctg tcctcttcta tgcccacagt aggaggagcc    4320
aggattggtt actccctgct gggtctgctg tgctcagagt gaggtagaga agtgggtaga    4380
gtaaagaatt tgggagagga aaaaaggcat tttcccaacc cctcccacca aagcctagag    4440
agaaggtgtt gtctggttta atgtttaatt agagctcaga gttcagggcc agatttggag    4500
ttgggatgga aagttgtttt taagaccctg tagcaatttt tgacccagcc tgggtacctc    4560
aaccacactc aggagtttgg gggaccttct gttgggctgg attataggct ccaagaagaa    4620 accccctttcg ccaatactct ctctctcttc ttttttgag acaggtctt gttctgttgc     4680 ccaggctggg gtgcagtggc atgatcacag ctcactgcaa cgtcagcctc acaggctctg    4740
gtgattctcc cacctcagcc tcctgagtag ctgggattac aagtgtgtgc caccatgccc    4800
agctaatttt ttttttcttt ttttttttt gagacggagt cttgttctgt tgccaggctg     4860
gagtgcagtg gtgcgatctc ggctcattgc aacctccacc tcccaggttc aagcgattct    4920
cctgcctcag cctcccgagt agctgggact acaggcacat gccatcacgc ccagttaatt    4980
tttgtatttt tagtagagtt ggggtttcac catgttggcc aggatggtct tgatctcttg    5040
acctcgtgat ccgtccacct tggcctccca agtgctggg attacaggtg tgagccaccg    5100
tacccggcca ctaattttta tatttttgt agagatgggg tttcaccgtg ttgcccaagc     5160
tggtctcgaa ctcctaggct caagtaatcc acctgccttg ccttggcct cccaaagtgc     5220 tgggatgtat aggcatgagc taccgcacct ggtaccccct gccccttctc tgtctctttc    5280
tagtctgtag cccaagggat ttggataccc aagtgcaggc agaatgggaa ggttgtaagc    5340
accagggaag cctgtctgga gtccaggctt gcagctgggc cccacccag gcaaggcagc     5400 tgggtggatg actcagatgc tgccccctc cctcccaccc tggtggcttt acagaagaca     5460
gcaggagaca gggtggagac agcagttgtc ttaaagggag gagtggtggt ctgaatgtct    5520
acctcttctg cccccctccc cattgcatcc tggagtccct tgcctggctc cttcctgaga    5580
ccctctggtg gtgtctggac acatagctct ctctggacag gtaacatgca caagtaatta    5640
gaatccagag ttgagttcag agttatggat tgggctgcag gatagtgcca gggtctgtgc    5700
cttcccatgt gaaactgatg gaggaaggct gagtcagaag tggggagatc cgaggcccac    5760
aaagcagaag cgctacttcc actccaaaaa ggccctggtg cttgacaact tcctggattg    5820
cccactgttg cagccccagt gtggacaggc agggagatgc aggctccagt tcatgtaggc    5880
tctgatcaag acaagaacag caaaggccac agaggcacag atgcttgtcc catgtcacac    5940
aataaagggg tcagcacttg atcacaggcc ttatgacttc cagctgggtg tgctcttacc    6000
attaagcctc acttctctag cttgggggac aggttggagg gaggatctag agggtgaggt    6060
aaggtgaagt caggtagctg aggctcactt ctgcagcctg gaaactctgc tctggggcca    6120
gtgacacctt agtgctctat ggccatactt cgtggctcat gcctgtaatc ccagtgcttt    6180
gggaggctaa ggcaggagga tcacttgagg ccaggagttt gagaccagtc tgggcaacat    6240
agcaagaccc ccttctgtac aaaaaaatta gccggtcaac acctgtagtc cagctgcttg    6300
ggaagctgag gcgggaggat cacctgaagc caggagtttg aggctattgt gagctatgac    6360
tgcactactg cactctagcc tgggagagag aaagaccctg tctctgaaaa agaaaaaaac    6420
aaaacaaaac tctgctgtcc tgcagggcct gttagcatat gatcgatagc ctttgctcca    6480
```

| | |
|---|---|
| gcctatacct ggacccagga cccctgccag cccctcaatc gtgagacggt cagagctctg | 6540 |
| ggaggctggt gattcttgtc ttgagactat cttgagactt gtcatgggaa ttgtccaccc | 6600 |
| ggattgaaag gaagctgtgc cttttggcag acccattagg ttaatggggt tggagacctt | 6660 |
| tgaggatgca tgggccctgg gctttatctg agggtatctc ctggtgttac ctctccaacc | 6720 |
| ctccaccacc aaatccattc tttttttttt tttttttttt ttttgacag tctcgctccc | 6780 |
| tggcccaggc tggagtgcag tggcatgatc ttggcttact gcaatctcca cctcccaggc | 6840 |
| tcaagtgatc ctcccacctc agcctcccaa gaagctggga ctataggcac gtgccacatg | 6900 |
| ctcggctaat ttttctattt ttagtagaga ccaggtttca ccatgttact caggctggtc | 6960 |
| ttgaactctg ggcttaagc agtccaccca ccttgacctc ccaaagtgct gagagccact | 7020 |
| gagcctagcc caaatccacg ttctgattca aagggaaaga agaagggtgc agctaaacct | 7080 |
| gggggggtgag aagtacttaa aaagcccaag agaaacaaaa gagagaataa ttcctcacta | 7140 |
| ggaccccta ttgccttccc actattggtg cccttgcttg gcacttcccc tggcctccag | 7200 |
| gagtctgaga cttactcttc catggatgtg cccattgccc ccacttccag gtccacccc | 7260 |
| cagtgattcg gtagcttagt gtctgcgctg aagcccagga cagctggatg gacaactggt | 7320 |
| agatcccttc acctaccaac tgtgctttct gctcccctcc cccttgcttc cctcctcccc | 7380 |
| agcccctcgc caccctagc agctgcagca gccaagacca agtcttcaga gcccagaca | 7440 |
| caagggcagg gttcattcca ttctcacctc cttggggtcc cagtgtactg ataggccgaa | 7500 |
| ctctaatatt ataggagatc tctggaagat tgcagggtct cttatccctc aataagggc | 7560 |
| aaggcaagcc gggcgcagtg gctcacgcct gtaatcccag cactttgaga agccagggg | 7620 |
| aacagatcac ttcaggtcag gagttaagag accagcctgg ccaacatggt gaaaccctgt | 7680 |
| ctctactaaa aatacaaaaa ttaaccagaa atcgcttgaa cccaggaggc agatgttgca | 7740 |
| gtgagccgag atcacgccac tgcactccag ccagggcgac agagcaagat tccgtctcaa | 7800 |
| aaaaataata ctaataataa ataaataaat aaggggcaag gtagtccacc aacaaaatga | 7860 |
| caggcagtgt gatatagtgg acaccctagc cctcggtgcc cttagttctg tgtgtggccc | 7920 |
| tttcactaaa ttgctgtgtg accttgagca aatcgcctcc cctttctggc tttccttagc | 7980 |
| tgtaaaagaa agggattgga gcggaaagtc tccagagacc ttttaggttc caaagtagta | 8040 |
| cagtgaccca caaagtgaga aaacagtctt ctaaaatacc aagttattaa tagtaaaatc | 8100 |
| aaatataaat aatgtgaata tagttaatag ctaatgttgt tctcaataga atgtttccc | 8160 |
| acaagctgtg gaattaaaca tactaccaca tttctctatt tccccgtgaa agtttgttag | 8220 |
| aaatggttaa attgtgacat taccctcttg gcaaatgttt tgttttcatt gctactagga | 8280 |
| aagggcaact cgttttcgat gcctctccct tctggacggt ggaaagggct gtgtcataga | 8340 |
| gtaggaacgg gagatgcggc acaggaatgg ctcccattga cccgggttgg gggctagggc | 8400 |
| gaaggcctag gagaggcaga actgttacct tagagctggc caggattaga gaacagtgcc | 8460 |
| tggaaccggg gggaggggca cggtgacctt gggctgccca ccttctaccc ttccagcacc | 8520 |
| catactggct ccccccaacct gcggctgggc tgggaggagg tcttggcccc taccaatccc | 8580 |
| ttaaggaagg ggaaagagtt tgggaagggg agtcctcct tcacccctgc ctcccccaag | 8640 |
| ttgtgagaga ggaagccgga atcctgcctg ctgaagccag gaataattct ggctgagatc | 8700 |
| ccaggcccgg caggggcgct gagtcatggt agagggcaga gtggagagtg gacaggagac | 8760 |
| cctaagcttg tccagtcaga aaagcagagg ctgaggggtg gccttttctt gagaactaca | 8820 |

```
ttcaagttgc agcaagaagg acagtggtct gaatttgacg gggacaaatg gaagggagat   8880
aggacacatg agttccttta ggtctggctc aggggagcta gacttcattt caagggtct    8940
aggttctggg cagttgagaa ggaggctatt tggggtcacc aaggctcccc tttcttccca   9000
aagctctaac actgccacct tctgctggct aggagagagc tgtgtcttct gaggctagag   9060
ctggaatgca gtgagaccag actgcctagg tcctccctca cttcttctcc tgaccttggg   9120
gtgtggctcc cactctctcc cagtgtcctc agggttaata actatgtgcc accagataga   9180
gagttaaggg gctgctgaat tggcttcttg tgaagggaat cccctaaatg tccctcgttt   9240
tggtcactgg cctccctccc gcccccttca ggacattcta ctatcttctt aggccatccc   9300
tccctcctcc aggcactact tcttttgctc tatccccaag ccccacccct gcattttgt    9360
gacaacaccg gaatgatttc tagagagaga ggccaggaag aaggaaagtg gcacttggca   9420
ggagaccttg caggggggcgg ctggtgagga agccagccgc ccattgtcca ggaccccagt  9480
gccctggcct ccggcctcag gcttctcctg cctctgtaca atgccacgtt gatacgccca   9540
gcagctgtga ctcaggcctg gcccctgcc aggcccagca cttctactgg agttgcgtct    9600
gaacatgtca acaggcttcc tatccctctc tcagcaccag ttctccccac ttcagcccct   9660
ccctctgcct ggaattaaaa cctggctttg tcttagggaa ggacagctgg gagcctagtg   9720
gctctggtag gggatctgag aggcctcaga ccctaggcat atttggctgt ttggcaggtg   9780
tcacgcccaa gggaagcgtg tggaagcaga gccatgcctg ctgtgggtgc acatgcccgc   9840
gtgagggagt cggggtgttt catcctgggg cacctgtggg cttttgaggt gtatgatatt   9900
cagaacttca caggttgggg tttggggaag gctcaagggg cttctaagtc cctggaacag   9960
ctgccccct cagttcctct ctctctctct ctttttttt gagatggagt ctcgctctgt    10020
tgcccaggct agaatgcagt ggcgcgatct tggctcactg caaactccgc ctcctgggtt   10080
caagtgattc tcctgcctca gcctcccaag tagctgggac tataggtgcc cgccaccatg   10140
cctggctaat ttttgtattt ttagtagaaa tggggtttca ccatgctggc caggatggtc   10200
tcaaactcct gacctcgtga tccacccacc ttggcctccc aaagtgctgg gattacaggc   10260
gtgagccact cgcgccagcc tcagttcctc tctttaaggt ctccttccca gagagggata   10320
gcacctcaaa tgccagggag gggaattctc cacatcctgc ccttacccga gttgtggcag   10380
acccacagac tagccaagaa accaagcagt ggttactttg ccgggttggg ggggaggtag   10440
gggctatcaa acctcatgat tggccgcaca caaaggtgtg agtatgtgta tatttgaggg   10500
tgggtgggag tggcactttc actaggcctc cgtatcactc tctgactggg gtatctccca   10560
gcaagcgaga cagaggcaga cacgcttccc agactgtctt actgggtctc tctgtgttat   10620
tctctgcagt gtctgtgtgt atcgtgccat tttctatgtt ttgcaccaat ctgctgtgag   10680
tgtcctcagg tgacctgggg gcaggttttt agtgcctgag cctacccgtc tccaggcttt   10740
agtttccccc tgtaaaagta taggagttgg ttcaagagaa ggttcctcta gaagccttga   10800
gcctgtgaac cgtctagtct ccgggtattt gtgggacaca cagaaaaagc cccacgaccc   10860
aacaggtaga acactggctg aaatcagcag ggcagagctg agacaggctc aagtaggctg   10920
aggggtaggg aggttttggg tgaatggagg ggagggacag agagaaggag gatatattgc   10980
agtaggagga gttgctggaa caaaggagg ggtggtagga gtggcttggg gtggcagcag    11040
aagacgccct gtcacatggc gggaagtcag cctgggcaga ggtctaggtg tccaggaggg   11100
gctgggtgtg gtggctcacg cctgtaatcc caggactttg ggaggctgat gcaggaggat   11160
cacgtgaggt caggagttca agaccagcct ggccaacatg gcgaaaccct atctctacta   11220
```

```
aaaatgccaa aaattagctg ggtgtggtgg caggcgcctg taatcccagc tactctggag    11280
gctgaggcac aagaattgct tgaacctggg aggtggaggt tgcagggagc cgagatcgcg    11340
ccactctact ctagcctggg caacacagtg agactctgtc tcaaaaataa taataatagg    11400
ggctgggcgc ggtggctcat gactgtaatc ccagcatttt gggaggtgga ggcgggtgga    11460
tcacctgagg tcaggagtcc gagaccagcc tggccaacat ggcaaaactc cgtctctact    11520
aaaaatagaa aaattagcta ggcatggtgg tgcaggcctg taatccagct actcgggagg    11580
ctgagaagca ggagaatcac ttgaacctgg gaggtgaagg ttgcagtgag atcacctggg    11640
cgacagaatg agactccacc tcaaaataat aataatagta ataataataa atgaaaaatt    11700
ttaaaattaa acaattaaaa attttaaatt aaaattaaac aaattagatg cccaggagga    11760
tacaggagag catttgccac caggcggact ccctgtaccc acccggccac agggggcgat    11820
gttcctggga gacaggaaat gcccaggggc tgggagaccc tctgctcttc tgctcccttc    11880
ctgtgtgctg cctggcaatg gggaactctg agggctggtg agcagggctg ctgaggagtg    11940
ggtctaagga gtccctgcag ggctgggcca gctcctccac ctcccctttg tcttcccctc    12000
ccacttgtta ttttagcta cagtgtctgt ccctcttgct tctcccccag attgggagag    12060
gaaacggagg cctctccctc cgggcctagc ctgttgcccc cagcaaccgg gcccaaacag    12120
gcctgtggcc ggccctggct tccatatctg gcatcagagt tgggctgagc agggtgactc    12180
agagggtggg tcagcgcctg gccggtgcc cacctagccc ctttgctgtg ctggtgcctt    12240
tcttccccaa acagcccaa gggcccgggc ctgctgcagc tggggagccg gacttccttg    12300
tcccaccagg cacagctctt cagacccctg ccttgggtca catttgcaag tgccaactct    12360
catttctacc ttattctttt cctctctgtt cccctcccca cccctctct tccctctttc    12420 tgagatcaga tttgccagtg atgggaagag ttagaaacag gatgcccagc ccttctcgcc    12480
tcaagaggcc actgggatgc agccactcct gtgcttgggg aacctggagg atgcaaggga    12540
aaggactggc actctgctgg cacagcaccc ggcctggggc aggacacggg cgaagccagg    12600
gtctcccctg tgagcactag aggatttccc gaccnctgcc cgggtattgt gtgcctgagc    12660
atgagtcacc tgagggccc aggttcccac ccttcccagc tcctctggcc tgccccaccc    12720
tgtcctccct gccaacccag cacggggacg gcactcagcg tgtgctcagc tttcctgatg    12780
ccaaccccca gtggagtggg ctgcaccacc accctgggac cgaatgcctg gctagggtct    12840
actttggtcc ctgctaggtc tgaggacccc tcctaggaag gaaatggcac ttgggggcgg    12900
gggcagggag gagggaggag agacactggg ctctactgta cccctagtca tctcttgggg    12960
tgtgcgtgtg gctccctggc cacagagctc ccaaggtctg agtcatgagc ccatgggtga    13020
tagtggcttc ttcccccgcag atgggagctc cccgtgccta agaaaaccac aaaggttctt    13080
cctcacttcc ctctctgctc gtggtttttc tcatctgcag ggtgtgtctt agtcctttaa    13140
tctcctctct ttgcagtgct agtcaaaacc tccaccaggg aaagacaaat aaccccctta    13200
ctgttttttt tttttttttt tttttttttt gagatggagt ctcgctctgt cacccatgct    13260
gtagtgcagt ggcacaatct cggctcactg caacctccgc ctcccaagtt caagtgatcc    13320
tcctacctca gcctcctcag tagctgggac tacaggtgca caccaccgta cccagctaaa    13380
tttttttttt tttttttga gatagagtct cactctgtca cccaggctgg agtacagtgg    13440
tacaatctca actcactaca atctccgcct cccaggctca agcaattctc gtgtctcagc    13500
ctcccaagtt gctgggacta tggacgtgca ccaccttgcc cgactaattt ttgtattttt    13560
```

```
gatagagtca gagtttcacc atgttggcag gctggtctcg aactcctggc ctcaagtgat    13620
ccacctgcct tggcctccca aagtgctggg attacaggtg tgagccacca cactcagcca    13680
gcccccttac tttccttgga gaccatatac tgtggcttgt gccaaagtgg tacagcatgg    13740
atttccagct cccctatcta cttgctgcgg gaccctagat atagctttct gtgcctattt    13800
cctcaattgc ataggaatag cacctatcgc atagggtagc tgtgaagatg acgtgagtta    13860
acataatatt tagagcagtg cttggtacct aataagctct atataagtgt ttgctattat    13920
attattatta tcactgccac caccgctttt gcaagcagca gaaggtgaag aggttagact    13980
gaagaaaaaa cttctgtgct catcagccca taagctcgca gagcacaggg atcatgcatc    14040
tatgttttcc tcagtcagtg tctgccaggc actggcaagg aaaggctgtt accaggggga    14100
actccaggaa ttcctcctgg cacctaagga ggctggggag acaggactag ggaaaaggtg    14160
cccttgagac accttctgaa atcatcccat tgccttccag cttctttcag ctcaggctgg    14220
ctggtcaggg aaacgctttg tgccatagtg tctgccctct tcctcctcct ggcttctcca    14280
ttctctctgg aacttgtggc ttaggaaagc agtgaggtgg aggaggagga accctagatc    14340
agcagctaga attgactgga atgctgctgc tggctttcgg taattgacac tgggccattc    14400
accttcctcc tttgcaccte agtttcctca tctataaaag ggagagggtt gagctgaatc    14460
aactctaagc tccttctagt tctctaaatt ctgagagcct cctagtacag ccagcagcag    14520
ccattagcct tcagggtaga gaggcctctt ctggaagcc ccagccagcc tgggggtcag     14580
cccaaggagc tcggaatcta agttgcccca gttgcttcac tttaccagcg gttttttcttc   14640
attttccctc ctccccctgc agctgcttca gcttcggaaa agttctgaag tcatggaaag    14700
ttggggctgt gctcccagcc aggggctagg ccggatggca gccaaaacct gagctgggtt    14760
ttgactttat ttttagcttt tctgactgag acagaggagg gaatacattc tccggttctg    14820
gaagggctc ttttttgcag gagacagaca cttacattaa acaacttgtt ctgaggtgtg     14880
gccagaggcc tggactgagc aagtgtgcag gctgggggag cttcctctgg cttctcatgt    14940
ccttcccctg cccctctgag tgtcactcta tcctcctccc tgcctggtgg ggggaggtgg    15000
gggtgactcc ttttttggac tctcctaagc agaacactgc ctgggtctcg tcctccagag    15060
cttctgcaaa tctagccttc cctatccctc ttcacagtga attgctgggc ctcttggagt    15120
ttaggacttt tgtggtagaa gaaaaatgtt ggcagggctg cttttctcct ttccaggata    15180
gatttttcct tctgcccacg cttggttttc ctttttttcca tctgctgtgg tgggctcatg    15240
cttaagcact gatgagttac agatggcagc tggaaccagg tcctctggat cttccctcc    15300
gctccctggg tctgctgctt tctctcaccc tatatttgtg aagcaattgt aacatctaga    15360
aagttcttgg gttctctgga ggttttaag aaaataggac cttttctattt ctccagtcca    15420
ctagcaaaaa taatcagggg cccagaaaag gtgagggagg tggcagaggc agcgctgttc    15480
gactggttat agctaaagct ttacccactt tgaggagcag ggaggcttaa agctggggcc    15540
cagatggacc tggaggcctg ggatccacat ctggaaccag atgctgaggc tatggtagat    15600
gggtagggct cagccttctc ccagggcacg gatgaggcag gagggaggga ggcagggacc    15660
cctctgttca gtgcagatca gggcacccag actgggtcct gagaaaggaa agggtcaata    15720
ttgtgcctgg tcatccttgt ctgaggtccc tctgagctct aaccagactt ccttcccca    15780
cagtcccaca tgtgtaaaag ggactaggag aggtgaccag tacctttggg gctcagatcg    15840
agaagtgcta gggacatgtg ggccatgagc ttagttgtca ggctcctcag agggaggaa     15900
gcttggccaa agggaagtga gtagagtcca gggagaaggc taagtaaggc cctgtgtggg    15960
```

```
aaggggcagg agacaaaggt acccctgtct ctttgggaaa gaatgggagg agagagaggg    16020
aaaagcattc atatcacggg gtagagctct gcccttggcc ccaggcacgt tcctgagccc    16080
tgagtcatgg gaagggtgga gaagcaggaa gggggttttc aaggaccttg gggaggtggg    16140
agcccagccc cagaggcaag cagatgcaaa ccaacctaat gcaaggatgc cctctcctgg    16200
taattgcagg catagcagcg ccagccccca tggctgacct cctgggagcc tggcactgtc    16260
taggcacaca gactccttct cttaaatcta ctctcccctc tcttctttag caataccaag    16320
aaggagggtg acctgatagc tgctcaggct cggctgaagg acctggaggc tctgctgaac    16380
tccaaggagg ccgcactgag cactgctctc agtgagaagc gcacgctgga gggcgagctg    16440
catgatctgc ggggccaggt ggccaaggtg aggccaccct gcagggccca cccatggccc    16500
cacctaacac atgtacactc actcttctac ctaggccctc ccccatgtgg tgcctggtct    16560
gacctgtcac ctgatttcag agccattcac ctgtcctaga gtcattttac ccactgaggt    16620
cacatcttat cctaatttgg ctgccaatgg gatctaccac agtgaattta aaataatcca    16680
ggaggccggg catggtggtt cacgcctgta atcccagcac tttaggaggc cgaggtgggc    16740
cgatcacgag gtcaggagat cgagatcatc ctgactaaca tggtgaaacc ccgtctctac    16800
taaaaataca aaaaattagc ctggcatggt ggcgggcgcc tgtagtccca actactcggg    16860
aggctgaggc aggagaatgg cgtgagcctc gaggcagag cttgcagtga gctgagatca    16920
tgccactgca ctccagcctg gcaacagag tgagactccg tctcaaaaaa ataataataa    16980
taataataaa aataatccag gccatgtgtg gtggctcatg cctgtaatcc cagcattttg    17040
ggaggccaag gaggcaggat tgcttgagtc caggagtttg agaccagcct gggcaacaca    17100
gaccccatct ctagaaaata aaaatttaaa gaaattagct gggcatggtg gtgtgcacct    17160
atagtcccag ctacttggga ggctgaggca ggaggatggc ttgaacctga gaggtcgagg    17220
atacagtgag ctgtgattgc accactgcac ttcagcctgg gtgacagagg gaaaccctgt    17280
ctctacataa ataaatacat aaaataaaat aatccacaag ccatttctac ttaactttgc    17340
aatgaactgt acctgaccct agatccctcc cagtttggcc ctccggtata caagggcctc    17400
ctataggccc ttgtgatttc tctggggaaa aggaggactg gagttgatca tttattgagg    17460
ccatcagaag cggatggcta attacatatg ggacatgtgt taataatgct ttgtgtatat    17520
agagtggcct ttactttcaa aacactcttc tccaatttat catgttaaaa gctaggaatt    17580
gggctgggtg cagtggctca cgcctataat cccagcactt tgggaggcca aggcgggtgg    17640
atcatttgag gtcaggagtt tgagaccagt ctgaccaaca tggttaaact ccgtctctac    17700
taaaaataca aaattagcca ggcgtggtgg cacacacctg tagtcccaac aactacttgt    17760
gaggctgagg caggaaaatc atttgaaccc aggatcagag gttgtggtga actgagattg    17820
caccattgca ctccagcctg gcaacaagag caaaactct atctcaaaaa aataaaaaa    17880 tagccaggca cggtggctca tgcctgtaat cctagcactt ggaggcag aggtgggcag    17940 atcacctgag gttaggagtt cgagactagc ctggccaaca tggtgaaacc ccatctctac    18000
tacaaataca aaaattagct aggcatggtg gcagccacct gtaatcccag ctacttggga    18060
ggctgaggca ggagaatcgc ttgaacccgg gaggtggagg ttgcagtgag ccaagatcgg    18120
gtcacagcac tccagcctag gcaacagagc gagactccat ctcaaaaaaa cataaataaa    18180
taaaaataaa aataaataat aaataaaagc taagaatcaa agaagcagtt tattcctaat    18240
ttcacagtct catctgttca tagtggggcc aggattagag tcagtggcca agcttccatc    18300
```

```
ctgggttctt tcccttccca ggccctacca tcatagtata ccagggaaag acctggagaa    18360
gccagcaggt tgaccaccga accaaggctg ggccaccttc ctcctgggtc tggtctccag    18420
cctcccagtt gtacccttcc cccagccctt cctggatgca ctgatcagcc tgtgcttcct    18480
tgccctgttt ttctttataa atagagccat gttctcctct ctctctctct cttttttttt    18540
tttttttttt tgagatggag tcttactctg tcacccaggc tggagtgcaa tggcacgatc    18600
tcagctcact gcaacctctg tctcccaggt tcaagcaatt ctcctgcctc agcctcccga    18660
gtagctggga ttacaggtgc ccaccaccat gcccagctac ttttttggatt tttagtagag    18720 acagggtttc accatgttgg tcaggctggt cttgaactcc tgaccttagg tgttctgccc    18780
gcctcagcct cccaaagtgc tgggattaca ggcgtgagcc accacgcctg gcaagacgtg    18840
ttctctctat gttgttgagg ctggtcttga actcctggct gcaagagatc ttcctgcctc    18900
agcctcccaa tgtgctggga ttataggcat gagccaccac acttagccca gcctgtgctt    18960
tcttaaatga aaatctaagc atacggctgg gtgtggtggc tcacgcctgt aatcccagca    19020
ttttgggagg ccaaggtggg cagatcacga ggtcaggaga tcgagactat cctggccaac    19080
atggtgaaac cctgtctcta ctaaagatac aaaaattagc tgggtgtggt ggcccatgtc    19140
tgtagtccca gctactcggg agactgaggc aggagaatgg catgaacctg ggaggcagag    19200
cttgcagtga gctgagatcg cgccactgct ctccagccta ggtgacagag cgagactcca    19260
tctcaaaaaa aaaataaaaa taaaaaaaag aaaatctaag cgtggtgctc ccctgctcaa    19320
acatcctcag gttcttttca tggcagataa gggcatctct tcatgagcca gccctgcct    19380 actgacccag ccacctctcc catcccttcc caccccgtac ttcaggcttc agcagtactg    19440
atctttccaa agaccccaga acacacatgc cttcatacct ctgtgcctgt acatgcttgt    19500
ttctgccctt gaaatcatga cagtagctct ctgtaggccc cgctagcctg tcccttgggt    19560
cttagcctct tggaggcctt cccagagccc ccaaaagta ccccaggcat actttggttc    19620
cttctctcat gtcccctcag tactttgcac atacctcctt tatagcagtt gctatgttgt    19680
gccagagaag ggagtcctgt ggctggggg catatatctt ttcttttga gacagagtct    19740 agctgtgtca cccaggctgg agtgcagtag tgcgatctcg gctcactgca acctccacct    19800
cctggattca agcgattctt gtgcctcagc ctcctgagta gctgggacta caggcgtgtg    19860
ccaccatcat gcctggctac ttttttgtat tagatatata ttttctctct tagcacagta    19920
cctaccaaga gtgagtgagt agatgtcctg accccctgcag gcatccaagg ccctccttcc    19980
ctggacctgt ttccacatgt gtgaaggggt gcacaggcag cagcccacct ctcagcttcc    20040
ttccagttct tgtgttctgt gacccctttt cctcatctct gcctgcttcc tcacagcttg    20100
aggcagccct aggtgaggcc aagaagcaac ttcaggatga gatgctgcgg cgggtggatg    20160
ctgagaacag gctgcagacc atgaaggagg aactggactt ccagaagaac atctacagtg    20220
aggtggggac tgtgctttgc aagccagagg gctgggctg ggtgatgaca gacttgggct    20280
gggctagggg ggaccagctg tgtgcagagc tcgccttcct gagtcccttg ccctagtgga    20340
cagggagttg ggggtggcca gcactcagct cccaggttaa agtggggctg gtagtggctc    20400
atggagtagg gctgggcagg gagccccgcc cctgggtctt ggcctcccag gaactaattc    20460
tgattttggt ttctgtgtcc ttcctccaac ccttccagga gctgcgtgag accaagcgcc    20520
gtcatgagac ccgactggtg gagattgaca atgggaagca gcgtgagttt gagagccggc    20580
tggcggatgc gctgcaggaa ctgcgggccc agcatgagga ccaggtggag cagtataaga    20640
aggagctgga gaagacttat tctgccaagg tgcttgctct cgattggttc cctcactgcc    20700
```

```
tctgcccttg gcagccctac ccttacccac gctgggctat gccttctggg gatcaggcag 20760
atggtggcag ggagctcagg gtggcccagg acctggggct gtagcagtga tgcccaactc 20820
aggcctgtgc ctccacccct cccagtcacc acagtcctaa ccctttgtcc tcccctccag 20880
ctggacaatg ccaggcagtc tgctgagagg aacagcaacc tggtgggggc tgcccacgag 20940
gagctgcagc agtcgcgcat ccgcatcgac agcctctctg cccagctcag ccagctccag 21000
aagcaggtga taccccacct cacccctctc tccaggggcc tagagtctgg gccggatgca 21060
```

```
ggctggaagc ccagggttgg gggtgggggt gggggtggga ggttcctgag gaggagaggg 21120
atgaaaagtg tccccacaac cacagagaag ggtcgcagga tgtggagtca gatggcctgt 21180
gtgctgtttc tgtacactct tacctcacct tcacttctca gggctttggt tttcccattc 21240
gaaaatggag gctgttctta atctccctaa ctcagagttg ccacaggact ctgcaatgtg 21300
aggtgttaaa agcatcagta tttttctagt tggctgtgct atttgtgaca ggagaaaaag 21360
tctagcctca gaacgagagg tttcagttag acaaggggaa ggacttccca gttgccagcc 21420
aagactatgt ttagagcttg tgatgttcag agctggctct gatgagggct ctggggaagc 21480
tctgattgca gatcctggag agagtagcca ggtgtctcct acaccgaccc acgtccctcc 21540
ttccccatac ttagggccct tgggagctca ccaaaccctc ccacccccct tcagctggca 21600
gccaaggagg cgaagcttcg agacctggag gactcactgg cccgtgagcg ggacaccagc 21660
cggcggctgc tggcggaaaa ggagcgggag atggccgaga tgcgggcaag gatgcagcag 21720
cagctggacg agtaccagga gcttctggac atcaagctgg ccctggacat ggagatccac 21780
gcctaccgca agctcttgga gggcgaggag gagaggtggg ctggggagac gtcggggagg 21840
tgctggcagt gtcctctggc cggcaactgg ccttgactag acccccactt ggtctccctc 21900
tccccaggct acgcctgtcc cccagcccta cctcgcagcg cagccgtggc cgtgcttcct 21960
ctcactcatc ccagacacag ggtgggggca gcgtcaccaa aaagcgcaaa ctggagtcca 22020
ctgagagccg cagcagcttc tcacagcacg cacgcactag cgggcgcgtg gccgtggagg 22080
aggtggatga ggagggcaag tttgtccggc tgcgcaacaa gtccaatgag gtaggctcct 22140
gctcagggtc taaggggata cagctgcatc agggagagag tggcaagaca gaaggatggc 22200
atgtggagag aggaacatcc ttgccctcag agggtggacc agggtgagcc tgtatatctc 22260
ctccacactc tggttccagg cctggctcct ggactctttg gctgtgagac cttgagcagg 22320
ttatttaacc tctcagagca tcagtttcct catctgtaaa atggggatga atactgatcc 22380
ctaagtcttt gagttgtcag gaagatgaaa gataaggtat ccgtgtgcct ggtgctgcgt 22440
atgtgtccac agatcatggc tattatcccc gggggaaggg cagtgacagg ggtgtgtgta 22500
gatggaagga gaggcctcaa ttgcaggcag gcagagggct gggcctttga gcaagataca 22560
cccaagagcc tgggtgagcc tccccgacct tcctcttccc tatcttcccg gcaggaccag 22620
tccatgggca attggcagat caagcgccag aatggagatg atcccttgct gacttaccgg 22680
ttcccaccaa agttcaccct gaaggctggg caggtggtga cggtgagtgg cagggcgctt 22740
gggactctgg ggaggccttg ggtggcgatg ggagcgctgg ggtaagtgtc cttttctcct 22800
ctccagatct gggctgcagg agctggggcc acccacagcc cccctaccga cctggtgtgg 22860
aaggcacaga acacctgggg ctgcgggaac agcctgcgta cggctctcat caactccact 22920
ggggaagtaa gtaggcctgg gcctggctgc ttgctggacg aggctccccc tgatggccaa 22980
catcggagcc agctgccccc aacccaagtt tgccaattca gggccccttt ctagagctct 23040
```

```
ctgttgcagg ctccagactt ctccacccag taggcaaacc aaaagatgct tcctcaacag    23100
cacaaggggt ggaagttaga cagtgaggat tgttaaaggc agagccatac tcctacccgg    23160
agagcttgac agtgtccctc tggggtggaa atgagttcct tagctccatc accacagagg    23220
acagagtaag cagcaggccg acaaagggc aggccacaag aaaagttgca ggtggtcact     23280
ggggtagaca tgctgtacaa cccttccctg gccctgaccc ttggacctgg ttccatgtcc    23340
ccaccaggaa gtggccatgc gcaagctggt gcgctcagtg actgtggttg aggacgacga    23400
ggatgaggat ggagatgacc tgctccatca ccaccacgtg agtggtagcc gccgctgagg    23460
ccgagcctgc actggggcca cccagccagg cctgggggca gcctctcccc agcctccccg    23520
tgccaaaaat ctttttcatta aagaatgttt tggaacttta ctcgctggcc tggcctttct    23580
tctctctcct ccctatacct tgaacaggga acccaggtgt ctgggtgccc tactctggta    23640
aggaagggag tgggaacttt ctgatgccat ggaatattcc tgtgggagca gtggacaagg    23700
gtctggattt gtcttctggg aaagggaggg gaggacagac gtgggcatg cccgccctgc     23760 ctctctcccc cattcttgtt gcatgcatat cctctcattt ccctcatttt tcctgcaaga    23820
atgttctctc tcattcctga ccgcccctcc actccaatta atagtgcatg cctgctgccc    23880
tacaagcttg ctcccgttct ctcttctttt cctcttaagc tcagtagc tagaacagag       23940 tcagagtcac tgctctggtt ctctgtcccc aagtcttcct gagccttctc ccctttatg     24000 tcttccctct cctcctccgg gccctagcc tcccaaaccc ccattgcccg ctggctcctt     24060
gggcacagaa ccacaccttc ctgcctggcg gctgggagcc tgcaggagcc tggagcctgg    24120
ttgggcctga gtggtcagtc ccagactcgc cgtcccgcct gagccttgtc tcccttccca    24180
gggctcccac tgcagcagct cgggggaccc cgctgagtac aacctgcgct cgcgcaccgt    24240
gctgtgcggg acctgcgggc agcctgccga caaggcatct gccagcggct caggagccca    24300
ggtgggcgga cccatctcct ctggctcttc tgcctccagt gtcacggtca ctcgcagcta    24360
ccgcagtgtg gggggcagtg ggggtggcag cttcggggac aatctggtca cccgctccta    24420
cctcctgggc aactccagcc ccgaaccca ggtgagttgt ctctgctttg tctccaaatc     24480
ctgcaggcgg tccctggtc atcgagggt aggacgaggt ggccttgcag gggggagagc      24540
ctgccttctc ttccgcagcc cggggagtg ggagcctcct ccccacagcc tgagtcctag     24600
acagcccacc tctgcatcct gcccctcttg tctgagcccc agactggagg gcaggggcag    24660
ggctggagtg tgagggatgg gggagatgct acctcccttc taggggccag gggagggagg    24720
gtctgggtcc aggccctgct gctcacacct ctctcctctg ttttctctct tagagccccc    24780
agaactgcag catcatgtaa tctgggacct gccaggcagg ggtgggggtg gaggcttcct    24840
gcgtcctcct cacctcatgc ccaccccctg ccctgcacgt catgggaggg ggcttgaagc    24900
caaagaaaaa taacccttg gttttttttct tctgtatttt ttttctaag agaagttatt     24960 ttctacagtg gttttatact gaaggaaaaa cacaagcaaa aaaaaaaaa agcatctatc     25020 tcatctatct caatcctaat ttctcctccc ttccttttcc ctgcttccag gaaactccac    25080
atctgcctta aaaccaaaga gggcttcctc tagaagccaa gggaaagggg tgcttttata    25140
gaggctagct tctgcttttc tgccctggct gctgccccca cccgggac cctgtgacat       25200 ggtgcctgag aggcaggcat agaggcttct ccgccagcct cctctggacg gcaggctcac    25260
tgccaggcca gcctccgaga gggagagaga gagagagagg acagcttgag ccgggcccct    25320
gggcttggcc tgctgtgatt ccactacacc tggctgaggt tcctctgcct gccccgcccc    25380
cagtccccac ccctgccccc agccccgggg tgagtccatt ctcccaggta ccagctgcgc    25440
```

```
ttgcttttct gtattttatt tagacaagag atgggaatga ggtgggaggt ggaagaaggg    25500
agaagaaagg tgagtttgag ctgccttccc tagctttaga ccctgggtgg gctctgtgca    25560
gtcactggag gttgaagcca agtggggtgc tgggaggagg gagagggagg tcactggaaa    25620
ggggagagcc tgctggcacc caccgtggag gaggaaggca agaggggtg gaggggtgtg     25680 gcagtggttt tggcaaacgc taaagagccc ttgcctcccc atttcccatc tgcaccccttc   25740 ctctcctccc caaatcaata cactagttgt ttctaccct ggctgctgtg gtgtctttgt    25800
tggtggacgt cgctgtgtgt actgaggtgc agactcgtgg gcatgcgcgc gcgtacacac    25860
acacacacac acacacacac acacacacac acacacacag cgccgcacgg tcactgcatc    25920
ctcctgctca ttgctgccca gccctgccct gctccagggg aaacaattag agatcagagc    25980
actttgggtg cacatctggg cactcggtgg tggctgaggg ggaaggcttt gatataacca    26040
tcaccaccca ctgtacggct ctctcccaac ggaagtcctt cagagaagca gcacctgaag   26100
gagggcattt gctaactaac ttccctcgtc caccagcact tactgagtgc tttctctgtg   26160
ctgggccctg agcg                                                     26174
```

```
<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccttaaaacc aaagagggct tc                                            22

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
catgtcacag ggtccccg                                                 18

<210> SEQ ID NO 10
<211> LENGTH: 22
<212> TYPE: DNA
<213> ORGANISM: Artificial Sequence
<220> FEATURE:
<223> OTHER INFORMATION: Probe

<400> SEQUENCE: 10
cttttctgcc ctggctgctg cc                                            22

<210> SEQ ID NO 11
<211> LENGTH: 20
<212> TYPE: DNA
<213> ORGANISM: Artificial Sequence
<220> FEATURE:
<223> OTHER INFORMATION: Antisense compound

<400> SEQUENCE: 11
gggctctggg ctcctgagcc                                               20

<210> SEQ ID NO 12
<211> LENGTH: 20
<212> TYPE: DNA
```

```
<213> ORGANISM: Artificial Sequence
<220> FEATURE:
<223> OTHER INFORMATION: Antisense compound

<400> SEQUENCE: 12
ccgagctgct gcagtgggag                                                    20

<210> SEQ ID NO 13
<211> LENGTH: 20
<212> TYPE: DNA
<213> ORGANISM: Artificial Sequence
<220> FEATURE:
<223> OTHER INFORMATION: Antisense compound

<400> SEQUENCE: 13
gcaggtcccg cacagcacgg                                                    20

<210> SEQ ID NO 14
<211> LENGTH: 20
<212> TYPE: DNA
<213> ORGANISM: Artificial Sequence
<220> FEATURE:
<223> OTHER INFORMATION: Antisense compound

<400> SEQUENCE: 14
tggcagatgc cttgtcggca                                                    20

<210> SEQ ID NO 15
<211> LENGTH: 20
<212> TYPE: DNA
<213> ORGANISM: Artificial Sequence
<220> FEATURE:
<223> OTHER INFORMATION: Antisense compound

<400> SEQUENCE: 15
gagccgctgg cagatgcctt                                                    20

<210> SEQ ID NO 16
<211> LENGTH: 20
<212> TYPE: DNA
<213> ORGANISM: Artificial Sequence
<220> FEATURE:
<223> OTHER INFORMATION: Antisense compound

<400> SEQUENCE: 16
ctgagccgct ggcagatgcc                                                    20

<210> SEQ ID NO 17
<211> LENGTH: 20
<212> TYPE: DNA
<213> ORGANISM: Artificial Sequence
<220> FEATURE:
<223> OTHER INFORMATION: Antisense compound

<400> SEQUENCE: 17
aggagatggg tccgcccacc                                                    20

<210> SEQ ID NO 18
<211> LENGTH: 20
<212> TYPE: DNA
<213> ORGANISM: Artificial Sequence
<220> FEATURE:
<223> OTHER INFORMATION: Antisense compound

<400> SEQUENCE: 18
cagaggagat gggtccgccc                                                    20
```

```
<210> SEQ ID NO 19
<211> LENGTH: 20
<212> TYPE: DNA
<213> ORGANISM: Artificial Sequence
<220> FEATURE:
<223> OTHER INFORMATION: Antisense compound

<400> SEQUENCE: 19
gccagaggag atgggtccgc                                            20

<210> SEQ ID NO 20
<211> LENGTH: 20
<212> TYPE: DNA
<213> ORGANISM: Artificial Sequence
<220> FEATURE:
<223> OTHER INFORMATION: Antisense compound

<400> SEQUENCE: 20
gagccagagg agatgggtcc                                            20

<210> SEQ ID NO 21
<211> LENGTH: 20
<212> TYPE: DNA
<213> ORGANISM: Artificial Sequence
<220> FEATURE:
<223> OTHER INFORMATION: Antisense compound

<400> SEQUENCE: 21
tggaggcaga agagccagag                                            20

<210> SEQ ID NO 22
<211> LENGTH: 20
<212> TYPE: DNA
<213> ORGANISM: Artificial Sequence
<220> FEATURE:
<223> OTHER INFORMATION: Antisense compound

<400> SEQUENCE: 22
acactggagg cagaagagcc                                            20

<210> SEQ ID NO 23
<211> LENGTH: 20
<212> TYPE: DNA
<213> ORGANISM: Artificial Sequence
<220> FEATURE:
<223> OTHER INFORMATION: Antisense compound

<400> SEQUENCE: 23
tgacactgga ggcagaagag                                            20

<210> SEQ ID NO 24
<211> LENGTH: 20
<212> TYPE: DNA
<213> ORGANISM: Artificial Sequence
<220> FEATURE:
<223> OTHER INFORMATION: Antisense compound

<400> SEQUENCE: 24
ccgtgacact ggaggcagaa                                            20

<210> SEQ ID NO 25
<211> LENGTH: 20
<212> TYPE: DNA
<213> ORGANISM: Artificial Sequence
<220> FEATURE:
```

```
<223> OTHER INFORMATION: Antisense compound

<400> SEQUENCE: 25
agtgaccgtg acactggagg                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense compound

<400> SEQUENCE: 26
ctgcgagtga ccgtgacact                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense compound

<400> SEQUENCE: 27
ggtagctgcg agtgaccgtg                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense compound

<400> SEQUENCE: 28
tctgggttcg ggggctggag                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense compound

<400> SEQUENCE: 29
ggctctgggt tcgggggctg                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense compound

<400> SEQUENCE: 30
gggctctggg ttcgggggct                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense compound

<400> SEQUENCE: 31
tctgggggct ctgggttcgg                                              20
```

```
<210> SEQ ID NO 32
<211> LENGTH: 20
<212> TYPE: DNA
<213> ORGANISM: Artificial Sequence
<220> FEATURE:
<223> OTHER INFORMATION: Antisense compound

<400> SEQUENCE: 32
agttctgggg gctctgggtt                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense compound

<400> SEQUENCE: 33
ctgcagttct gggggctctg                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense compound

<400> SEQUENCE: 34
ccagattaca tgatgctgca                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense compound

<400> SEQUENCE: 35
tggcaggtcc cagattacat                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense compound

<400> SEQUENCE: 36
tttcctggaa gcagggaaaa                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense compound

<400> SEQUENCE: 37
ccctctttgg ttttaaggca                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense compound
```

```
<400> SEQUENCE: 38
tctagaggaa gccctctttg                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense compound

<400> SEQUENCE: 39
tggcttctag aggaagccct                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense compound

<400> SEQUENCE: 40
cttggcttct agaggaagcc                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense compound

<400> SEQUENCE: 41
ctataaaagc acccctttcc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense compound

<400> SEQUENCE: 42
agctagcctc tataaaagca                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense compound

<400> SEQUENCE: 43
aaaagcagaa gctagcctct                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense compound

<400> SEQUENCE: 44
agggcagaaa agcagaagct                                               20

<210> SEQ ID NO 45
<211> LENGTH: 20
```

```
<212> TYPE: DNA
<213> ORGANISM: Artificial Sequence
<220> FEATURE:
<223> OTHER INFORMATION: Antisense compound

<400> SEQUENCE: 45
aggcaccatg tcacagggtc                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense compound

<400> SEQUENCE: 46
gcctgcctct caggcaccat                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense compound

<400> SEQUENCE: 47
ggctggcgga gaagcctcta                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense compound

<400> SEQUENCE: 48
tgagcctgcc gtccagagga                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense compound

<400> SEQUENCE: 49
atcacagcag gccaagccca                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense compound

<400> SEQUENCE: 50
ccaggtgtag tggaatcaca                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense compound

<400> SEQUENCE: 51
```

```
tggtacctgg gagaatggac                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense compound

<400> SEQUENCE: 52
ctggtacctg ggagaatgga                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense compound

<400> SEQUENCE: 53
agctggtacc tgggagaatg                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense compound

<400> SEQUENCE: 54
aaagcaagcg cagctggtac                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense compound

<400> SEQUENCE: 55
acagaaaagc aagcgcagct                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense compound

<400> SEQUENCE: 56
tcttgtctaa ataaaataca                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense compound

<400> SEQUENCE: 57
atctcttgtc taaataaaat                                              20

<210> SEQ ID NO 58
<211> LENGTH: 20
<212> TYPE: DNA
<213> ORGANISM: Artificial Sequence
```

```
<220> FEATURE:
<223> OTHER INFORMATION: Antisense compound

<400> SEQUENCE: 58
gcagctcaaa ctcacctttc                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense compound

<400> SEQUENCE: 59
ggaaggcagc tcaaactcac                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense compound

<400> SEQUENCE: 60
ctagggaagg cagctcaaac                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense compound

<400> SEQUENCE: 61
agagcccacc cagggtctaa                                                    20

<210> SEQ ID NO 62
<211> LENGTH: 20
<212> TYPE: DNA
<213> ORGANISM: Artificial Sequence
<220> FEATURE:
<223> OTHER INFORMATION: Antisense compound

<400> SEQUENCE: 62
cagtgactgc acagagccca                                                    20

<210> SEQ ID NO 63
<211> LENGTH: 20
<212> TYPE: DNA
<213> ORGANISM: Artificial Sequence
<220> FEATURE:
<223> OTHER INFORMATION: Antisense compound

<400> SEQUENCE: 63
agaaacaact agtgtattga                                                    20

<210> SEQ ID NO 64
<211> LENGTH: 20
<212> TYPE: DNA
<213> ORGANISM: Artificial Sequence
<220> FEATURE:
<223> OTHER INFORMATION: Antisense compound

<400> SEQUENCE: 64
tctgggctcc tgagccgctg                                                    20
```

```
<210> SEQ ID NO 65
<211> LENGTH: 20
<212> TYPE: DNA
<213> ORGANISM: Artificial Sequence
<220> FEATURE:
<223> OTHER INFORMATION: Antisense compound

<400> SEQUENCE: 65
ggctctgggc tcctgagccg                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense compound

<400> SEQUENCE: 66
ctgggggctc tgggctcctg                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense compound

<400> SEQUENCE: 67
ttctgggggc tctgggctcc                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense compound

<400> SEQUENCE: 68
gttctggggg ctctgggctc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense compound

<400> SEQUENCE: 69
tgcagttctg ggggctctgg                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense compound

<400> SEQUENCE: 70
atgctgcagt tctgggggct                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense compound
```

<400> SEQUENCE: 71
atggcatcag aaagttccca                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense compound

<400> SEQUENCE: 72
aggaatattc catggcatca                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense compound

<400> SEQUENCE: 73
tcccacagga atattccatg                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense compound

<400> SEQUENCE: 74
gatatgcatg caacaagaat                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense compound

<400> SEQUENCE: 75
ggagcaagct tgtagggcag                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense compound

<400> SEQUENCE: 76
ctctgagctt aagaggaaaa                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense compound

<400> SEQUENCE: 77
aggcaggaag gtgtggttct                                              20

<210> SEQ ID NO 78

```
<211> LENGTH: 20
<212> TYPE: DNA
<213> ORGANISM: Artificial Sequence
<220> FEATURE:
<223> OTHER INFORMATION: Antisense compound

<400> SEQUENCE: 78
gaagggagac aaggctcagg                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense compound

<400> SEQUENCE: 79
gatttggaga caaagcagag                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense compound

<400> SEQUENCE: 80
aggatttgga gacaaagcag                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense compound

<400> SEQUENCE: 81
gcaggatttg gagacaaagc                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense compound

<400> SEQUENCE: 82
tgcaggattt ggagacaaag                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense compound

<400> SEQUENCE: 83
cccgcctgca ggatttggag                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense compound

<400> SEQUENCE: 84
```
accagggacc cgcctgcagg                                                     20

<210> SEQ ID NO 85
<211> LENGTH: 20
<212> TYPE: DNA
<213> ORGANISM: Artificial Sequence
<220> FEATURE:
<223> OTHER INFORMATION: Antisense compound

<400> SEQUENCE: 85
ccctcgatga ccagggaccc                                                     20

<210> SEQ ID NO 86
<211> LENGTH: 20
<212> TYPE: DNA
<213> ORGANISM: Artificial Sequence
<220> FEATURE:
<223> OTHER INFORMATION: Antisense compound

<400> SEQUENCE: 86
acccctcgat gaccagggac                                                     20

<210> SEQ ID NO 87
<211> LENGTH: 20
<212> TYPE: DNA
<213> ORGANISM: Artificial Sequence
<220> FEATURE:
<223> OTHER INFORMATION: Antisense compound

<400> SEQUENCE: 87
gtcctacccc tcgatgacca                                                     20

<210> SEQ ID NO 88
<211> LENGTH: 20
<212> TYPE: DNA
<213> ORGANISM: Artificial Sequence
<220> FEATURE:
<223> OTHER INFORMATION: Antisense compound

<400> SEQUENCE: 88
ctgcggaaga gaaggcaggc                                                     20

<210> SEQ ID NO 89
<211> LENGTH: 20
<212> TYPE: DNA
<213> ORGANISM: Artificial Sequence
<220> FEATURE:
<223> OTHER INFORMATION: Antisense compound

<400> SEQUENCE: 89
gttcctcctt catggtctgc                                                     20

<210> SEQ ID NO 90
<211> LENGTH: 20
<212> TYPE: DNA
<213> ORGANISM: Artificial Sequence
<220> FEATURE:
<223> OTHER INFORMATION: Antisense compound

<400> SEQUENCE: 90
tcttggcctc acctagggct                                                     20

<210> SEQ ID NO 91
<211> LENGTH: 20
<212> TYPE: DNA

```
<213> ORGANISM: Artificial Sequence
<220> FEATURE:
<223> OTHER INFORMATION: Antisense compound

<400> SEQUENCE: 91
tgcccagcct tcagggtgaa                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense compound

<400> SEQUENCE: 92
gaagctgctg cggctctcag                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense compound

<400> SEQUENCE: 93
caaccacagt cactgagcgc                                               20

<210> SEQ ID NO 94
<211> LENGTH: 20
<212> TYPE: DNA
<213> ORGANISM: Artificial Sequence
<220> FEATURE:
<223> OTHER INFORMATION: Antisense compound

<400> SEQUENCE: 94
cagccctgcg ttctccgttt                                               20

<210> SEQ ID NO 95
<211> LENGTH: 20
<212> TYPE: DNA
<213> ORGANISM: Artificial Sequence
<220> FEATURE:
<223> OTHER INFORMATION: Antisense compound

<400> SEQUENCE: 95
gagtgagagg aagcacggcc                                               20

<210> SEQ ID NO 96
<211> LENGTH: 20
<212> TYPE: DNA
<213> ORGANISM: Artificial Sequence
<220> FEATURE:
<223> OTHER INFORMATION: Antisense compound

<400> SEQUENCE: 96
ctgtagatgt tcttctggaa                                               20

<210> SEQ ID NO 97
<211> LENGTH: 20
<212> TYPE: DNA
<213> ORGANISM: Artificial Sequence
<220> FEATURE:
<223> OTHER INFORMATION: Antisense compound

<400> SEQUENCE: 97
ctgcgttctc cgtttccagc                                               20
```

<210> SEQ ID NO 98
<211> LENGTH: 20
<212> TYPE: DNA
<213> ORGANISM: Artificial Sequence
<220> FEATURE:
<223> OTHER INFORMATION: Antisense compound

<400> SEQUENCE: 98
agcagccgcc ggctggtgtc                                         20

<210> SEQ ID NO 99
<211> LENGTH: 20
<212> TYPE: DNA
<213> ORGANISM: Artificial Sequence
<220> FEATURE:
<223> OTHER INFORMATION: Antisense compound

<400> SEQUENCE: 99
ttggtgggaa ccggtaagtc                                         20

<210> SEQ ID NO 100
<211> LENGTH: 20
<212> TYPE: DNA
<213> ORGANISM: Artificial Sequence
<220> FEATURE:
<223> OTHER INFORMATION: Antisense compound

<400> SEQUENCE: 100
tgttcctctc agcagactgc                                         20

<210> SEQ ID NO 101
<211> LENGTH: 20
<212> TYPE: DNA
<213> ORGANISM: Artificial Sequence
<220> FEATURE:
<223> OTHER INFORMATION: Antisense compound

<400> SEQUENCE: 101
ggtaagtcag caagggatca                                         20

<210> SEQ ID NO 102
<211> LENGTH: 20
<212> TYPE: DNA
<213> ORGANISM: Artificial Sequence
<220> FEATURE:
<223> OTHER INFORMATION: Antisense compound

<400> SEQUENCE: 102
tggtgggaac cggtaagtca                                         20

<210> SEQ ID NO 103
<211> LENGTH: 20
<212> TYPE: DNA
<213> ORGANISM: Artificial Sequence
<220> FEATURE:
<223> OTHER INFORMATION: Antisense compound

<400> SEQUENCE: 103
ctcacgcagc tcctcactgt                                         20

<210> SEQ ID NO 104
<211> LENGTH: 20
<212> TYPE: DNA
<213> ORGANISM: Artificial Sequence
<220> FEATURE:

```
<223> OTHER INFORMATION: Antisense compound

<400> SEQUENCE: 104
gcagccccag gtgttctgtg                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense compound

<400> SEQUENCE: 105
gagactgctc ggagtcggag                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense compound

<400> SEQUENCE: 106
tggtctgcag cctgttctca                                               20

<210> SEQ ID NO 107
<211> LENGTH: 20
<212> TYPE: DNA
<213> ORGANISM: Artificial Sequence
<220> FEATURE:
<223> OTHER INFORMATION: Antisense compound

<400> SEQUENCE: 107
tgcggctctc agtggactcc                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense compound

<400> SEQUENCE: 108
tgctgttcct ctcagcagac                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense compound

<400> SEQUENCE: 109
gcttggtctc acgcagctcc                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense compound

<400> SEQUENCE: 110
tgatggagca ggtcatctcc                                               20
```

<210> SEQ ID NO 111
<211> LENGTH: 20
<212> TYPE: DNA
<213> ORGANISM: Artificial Sequence
<220> FEATURE:
<223> OTHER INFORMATION: Antisense compound

<400> SEQUENCE: 111
agagccgtac gcaggctgtt                                          20

<210> SEQ ID NO 112
<211> LENGTH: 20
<212> TYPE: DNA
<213> ORGANISM: Artificial Sequence
<220> FEATURE:
<223> OTHER INFORMATION: Antisense compound

<400> SEQUENCE: 112
aaggcgcagc cctgcgttct                                          20

<210> SEQ ID NO 113
<211> LENGTH: 20
<212> TYPE: DNA
<213> ORGANISM: Artificial Sequence
<220> FEATURE:
<223> OTHER INFORMATION: Antisense compound

<400> SEQUENCE: 113
gagtcctcca ggtctcgaag                                          20

<210> SEQ ID NO 114
<211> LENGTH: 20
<212> TYPE: DNA
<213> ORGANISM: Artificial Sequence
<220> FEATURE:
<223> OTHER INFORMATION: Antisense compound

<400> SEQUENCE: 114
ggtcaccctc cttcttggta                                          20

<210> SEQ ID NO 115
<211> LENGTH: 20
<212> TYPE: DNA
<213> ORGANISM: Artificial Sequence
<220> FEATURE:
<223> OTHER INFORMATION: Antisense compound

<400> SEQUENCE: 115
acagcggagt ggagctggcc                                          20

<210> SEQ ID NO 116
<211> LENGTH: 20
<212> TYPE: DNA
<213> ORGANISM: Artificial Sequence
<220> FEATURE:
<223> OTHER INFORMATION: Antisense compound

<400> SEQUENCE: 116
ctgccaattg cccatggact                                          20

<210> SEQ ID NO 117
<211> LENGTH: 20
<212> TYPE: DNA
<213> ORGANISM: Artificial Sequence
<220> FEATURE:
<223> OTHER INFORMATION: Antisense compound

```
<400> SEQUENCE: 117
ctgcttctgg agctggctga                                                    20

<210> SEQ ID NO 118
<211> LENGTH: 20
<212> TYPE: DNA
<213> ORGANISM: Artificial Sequence
<220> FEATURE:
<223> OTHER INFORMATION: Antisense compound

<400> SEQUENCE: 118
cgcgctttca gctccttaaa                                                    20

<210> SEQ ID NO 119
<211> LENGTH: 20
<212> TYPE: DNA
<213> ORGANISM: Artificial Sequence
<220> FEATURE:
<223> OTHER INFORMATION: Antisense compound

<400> SEQUENCE: 119
atcctgaagt tgcttcttgg                                                    20

<210> SEQ ID NO 120
<211> LENGTH: 20
<212> TYPE: DNA
<213> ORGANISM: Artificial Sequence
<220> FEATURE:
<223> OTHER INFORMATION: Antisense compound

<400> SEQUENCE: 120
gtcttgcggg catccccgag                                                    20

<210> SEQ ID NO 121
<211> LENGTH: 20
<212> TYPE: DNA
<213> ORGANISM: Artificial Sequence
<220> FEATURE:
<223> OTHER INFORMATION: Antisense compound

<400> SEQUENCE: 121
ggtgatgcga aggcgcagcc                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense compound

<400> SEQUENCE: 122
tgctgtgaga agctgctgcg                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense compound

<400> SEQUENCE: 123
ccaccctgtg tctgggatga                                                    20

<210> SEQ ID NO 124
<211> LENGTH: 20
```

```
<212> TYPE: DNA
<213> ORGANISM: Artificial Sequence
<220> FEATURE:
<223> OTHER INFORMATION: Antisense compound

<400> SEQUENCE: 124
tgggaaccgg taagtcagca                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense compound

<400> SEQUENCE: 125
ggcctcgtag gcggccttga                                                    20

<210> SEQ ID NO 126
<211> LENGTH: 20
<212> TYPE: DNA
<213> ORGANISM: Artificial Sequence
<220> FEATURE:
<223> OTHER INFORMATION: Antisense compound

<400> SEQUENCE: 126
gtccgcccac ctgggctcct                                                    20

<210> SEQ ID NO 127
<211> LENGTH: 20
<212> TYPE: DNA
<213> ORGANISM: Artificial Sequence
<220> FEATURE:
<223> OTHER INFORMATION: Antisense compound

<400> SEQUENCE: 127
cctgggctcc tgagccgctg                                                    20

<210> SEQ ID NO 128
<211> LENGTH: 20
<212> TYPE: DNA
<213> ORGANISM: Artificial Sequence
<220> FEATURE:
<223> OTHER INFORMATION: Antisense compound

<400> SEQUENCE: 128
gagccgctgg cagatgcctt                                                    20

<210> SEQ ID NO 129
<211> LENGTH: 20
<212> TYPE: DNA
<213> ORGANISM: Artificial Sequence
<220> FEATURE:
<223> OTHER INFORMATION: Antisense compound

<400> SEQUENCE: 129
cagatgcctt gtcggcaggc                                                    20

<210> SEQ ID NO 130
<211> LENGTH: 20
<212> TYPE: DNA
<213> ORGANISM: Artificial Sequence
<220> FEATURE:
<223> OTHER INFORMATION: Antisense compound

<400> SEQUENCE: 130
```
tgggtccgcc cacctgggct                                                     20

<210> SEQ ID NO 131
<211> LENGTH: 19
<212> TYPE: DNA
<213> ORGANISM: Artificial Sequence
<220> FEATURE:
<223> OTHER INFORMATION: Antisense compound

<400> SEQUENCE: 131
ccagaggaga tgggtccgc                                                      19

<210> SEQ ID NO 132
<211> LENGTH: 20
<212> TYPE: DNA
<213> ORGANISM: Artificial Sequence
<220> FEATURE:
<223> OTHER INFORMATION: Antisense compound

<400> SEQUENCE: 132
tggaggcaga agagccagag                                                     20

<210> SEQ ID NO 133
<211> LENGTH: 18
<212> TYPE: DNA
<213> ORGANISM: Artificial Sequence
<220> FEATURE:
<223> OTHER INFORMATION: Antisense compound

<400> SEQUENCE: 133
agtgaccgtg acactgga                                                       18

<210> SEQ ID NO 134
<211> LENGTH: 16
<212> TYPE: DNA
<213> ORGANISM: Artificial Sequence
<220> FEATURE:
<223> OTHER INFORMATION: Antisense compound

<400> SEQUENCE: 134
ggtccgccca cctggg                                                         16

<210> SEQ ID NO 135
<211> LENGTH: 16
<212> TYPE: DNA
<213> ORGANISM: Artificial Sequence
<220> FEATURE:
<223> OTHER INFORMATION: Antisense compound

<400> SEQUENCE: 135
ggtccaccca cctggg                                                         16

<210> SEQ ID NO 136
<211> LENGTH: 16
<212> TYPE: DNA
<213> ORGANISM: Artificial Sequence
<220> FEATURE:
<223> OTHER INFORMATION: Antisense compound

<400> SEQUENCE: 136
ggtccgctca cctggg                                                         16

<210> SEQ ID NO 137
<211> LENGTH: 18
<212> TYPE: DNA
<213> ORGANISM: Artificial Sequence

```
<220> FEATURE:
<223> OTHER INFORMATION: Antisense compound

<400> SEQUENCE: 137
cactggaggc agaagagc                                                    18

<210> SEQ ID NO 138
<211> LENGTH: 18
<212> TYPE: DNA
<213> ORGANISM: Artificial Sequence
<220> FEATURE:
<223> OTHER INFORMATION: Antisense compound

<400> SEQUENCE: 138
gacactggag gcagaaga                                                    18

<210> SEQ ID NO 139
<211> LENGTH: 18
<212> TYPE: DNA
<213> ORGANISM: Artificial Sequence
<220> FEATURE:
<223> OTHER INFORMATION: Antisense compound

<400> SEQUENCE: 139
gtgacactgg aggcagaa                                                    18

<210> SEQ ID NO 140
<211> LENGTH: 18
<212> TYPE: DNA
<213> ORGANISM: Artificial Sequence
<220> FEATURE:
<223> OTHER INFORMATION: Antisense compound

<400> SEQUENCE: 140
ccgtgacact ggaggcag                                                    18

<210> SEQ ID NO 141
<211> LENGTH: 18
<212> TYPE: DNA
<213> ORGANISM: Artificial Sequence
<220> FEATURE:
<223> OTHER INFORMATION: Antisense compound

<400> SEQUENCE: 141
gaccgtgaca ctggaggc                                                    18

<210> SEQ ID NO 142
<211> LENGTH: 18
<212> TYPE: DNA
<213> ORGANISM: Artificial Sequence
<220> FEATURE:
<223> OTHER INFORMATION: Antisense compound

<400> SEQUENCE: 142
gagtgaccgt gacactgg                                                    18

<210> SEQ ID NO 143
<211> LENGTH: 18
<212> TYPE: DNA
<213> ORGANISM: Artificial Sequence
<220> FEATURE:
<223> OTHER INFORMATION: Antisense compound

<400> SEQUENCE: 143
gcgagtgacc gtgacact                                                    18
```

<210> SEQ ID NO 144
<211> LENGTH: 18
<212> TYPE: DNA
<213> ORGANISM: Artificial Sequence
<220> FEATURE:
<223> OTHER INFORMATION: Antisense compound

<400> SEQUENCE: 144
ctgcgagtga ccgtgaca                                                18

<210> SEQ ID NO 145
<211> LENGTH: 18
<212> TYPE: DNA
<213> ORGANISM: Artificial Sequence
<220> FEATURE:
<223> OTHER INFORMATION: Antisense compound

<400> SEQUENCE: 145
agctgcgagt gaccgtga                                                18

<210> SEQ ID NO 146
<211> LENGTH: 18
<212> TYPE: DNA
<213> ORGANISM: Artificial Sequence
<220> FEATURE:
<223> OTHER INFORMATION: Antisense compound

<400> SEQUENCE: 146
gtagctgcga gtgaccgt                                                18

<210> SEQ ID NO 147
<211> LENGTH: 18
<212> TYPE: DNA
<213> ORGANISM: Artificial Sequence
<220> FEATURE:
<223> OTHER INFORMATION: Antisense compound

<400> SEQUENCE: 147
cggtagctgc gagtgacc                                                18

<210> SEQ ID NO 148
<211> LENGTH: 18
<212> TYPE: DNA
<213> ORGANISM: Artificial Sequence
<220> FEATURE:
<223> OTHER INFORMATION: Antisense compound

<400> SEQUENCE: 148
tgcggtagct gcgagtga                                                18

<210> SEQ ID NO 149
<211> LENGTH: 18
<212> TYPE: DNA
<213> ORGANISM: Artificial Sequence
<220> FEATURE:
<223> OTHER INFORMATION: Antisense compound

<400> SEQUENCE: 149
actgcggtag ctgcgagt                                                18

<210> SEQ ID NO 150
<211> LENGTH: 18
<212> TYPE: DNA
<213> ORGANISM: Artificial Sequence
<220> FEATURE:
<223> OTHER INFORMATION: Antisense compound

<400> SEQUENCE: 150
acactgcggt agctgcga							18

<210> SEQ ID NO 151
<211> LENGTH: 18
<212> TYPE: DNA
<213> ORGANISM: Artificial Sequence
<220> FEATURE:
<223> OTHER INFORMATION: Antisense compound

<400> SEQUENCE: 151
ccacactgcg gtagctgc							18

<210> SEQ ID NO 152
<211> LENGTH: 20
<212> TYPE: DNA
<213> ORGANISM: Artificial Sequence
<220> FEATURE:
<223> OTHER INFORMATION: Antisense compound

<400> SEQUENCE: 152
gctgcagtgg gagccgtggt							20

<210> SEQ ID NO 153
<211> LENGTH: 20
<212> TYPE: DNA
<213> ORGANISM: Artificial Sequence
<220> FEATURE:
<223> OTHER INFORMATION: Antisense compound

<400> SEQUENCE: 153
ctgctgcagt gggagccgtg							20

<210> SEQ ID NO 154
<211> LENGTH: 20
<212> TYPE: DNA
<213> ORGANISM: Artificial Sequence
<220> FEATURE:
<223> OTHER INFORMATION: Antisense compound

<400> SEQUENCE: 154
gagctgctgc agtgggagcc							20

<210> SEQ ID NO 155
<211> LENGTH: 20
<212> TYPE: DNA
<213> ORGANISM: Artificial Sequence
<220> FEATURE:
<223> OTHER INFORMATION: Antisense compound

<400> SEQUENCE: 155
cccccgagct gctgcagtgg							20

<210> SEQ ID NO 156
<211> LENGTH: 20
<212> TYPE: DNA
<213> ORGANISM: Artificial Sequence
<220> FEATURE:
<223> OTHER INFORMATION: Antisense compound

<400> SEQUENCE: 156
gggtcccccg agctgctgca							20

<210> SEQ ID NO 157

```
<211> LENGTH: 20
<212> TYPE: DNA
<213> ORGANISM: Artificial Sequence
<220> FEATURE:
<223> OTHER INFORMATION: Antisense compound

<400> SEQUENCE: 157
tgtactcagc ggggtccccc                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense compound

<400> SEQUENCE: 158
cgcaggttgt actcagcggg                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense compound

<400> SEQUENCE: 159
tgcccgcagg tcccgcacag                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense compound

<400> SEQUENCE: 160
caggctgccc gcaggtcccg                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense compound

<400> SEQUENCE: 161
gtcggcaggc tgcccgcagg                                              20

<210> SEQ ID NO 162
<211> LENGTH: 18
<212> TYPE: DNA
<213> ORGANISM: Homo sapiens

<400> SEQUENCE: 162
gctcttctgc ctccagtg                                                18

<210> SEQ ID NO 163
<211> LENGTH: 18
<212> TYPE: DNA
<213> ORGANISM: Homo sapiens

<400> SEQUENCE: 163
tcttctgcct ccagtgtc                                                18
```

```
<210> SEQ ID NO 164
<211> LENGTH: 18
<212> TYPE: DNA
<213> ORGANISM: Homo sapiens

<400> SEQUENCE: 164
ttctgcctcc agtgtcac                                                 18

<210> SEQ ID NO 165
<211> LENGTH: 18
<212> TYPE: DNA
<213> ORGANISM: Homo sapiens

<400> SEQUENCE: 165
ctgcctccag tgtcacgg                                                 18

<210> SEQ ID NO 166
<211> LENGTH: 18
<212> TYPE: DNA
<213> ORGANISM: Homo sapiens

<400> SEQUENCE: 166
gcctccagtg tcacggtc                                                 18

<210> SEQ ID NO 167
<211> LENGTH: 18
<212> TYPE: DNA
<213> ORGANISM: Homo sapiens

<400> SEQUENCE: 167
tccagtgtca cggtcact                                                 18

<210> SEQ ID NO 168
<211> LENGTH: 18
<212> TYPE: DNA
<213> ORGANISM: Homo sapiens

<400> SEQUENCE: 168
ccagtgtcac ggtcactc                                                 18

<210> SEQ ID NO 169
<211> LENGTH: 18
<212> TYPE: DNA
<213> ORGANISM: Homo sapiens

<400> SEQUENCE: 169
agtgtcacgg tcactcgc                                                 18

<210> SEQ ID NO 170
<211> LENGTH: 18
<212> TYPE: DNA
<213> ORGANISM: Homo sapiens

<400> SEQUENCE: 170
tgtcacggtc actcgcag                                                 18

<210> SEQ ID NO 171
<211> LENGTH: 18
<212> TYPE: DNA
<213> ORGANISM: Homo sapiens

<400> SEQUENCE: 171
tcacggtcac tcgcagct                                                 18
```

```
<210> SEQ ID NO 172
<211> LENGTH: 18
<212> TYPE: DNA
<213> ORGANISM: Homo sapiens

<400> SEQUENCE: 172
acggtcactc gcagctac                                                 18

<210> SEQ ID NO 173
<211> LENGTH: 18
<212> TYPE: DNA
<213> ORGANISM: Homo sapiens

<400> SEQUENCE: 173
ggtcactcgc agctaccg                                                 18

<210> SEQ ID NO 174
<211> LENGTH: 18
<212> TYPE: DNA
<213> ORGANISM: Homo sapiens

<400> SEQUENCE: 174
tcactcgcag ctaccgca                                                 18

<210> SEQ ID NO 175
<211> LENGTH: 18
<212> TYPE: DNA
<213> ORGANISM: Homo sapiens

<400> SEQUENCE: 175
actcgcagct accgcagt                                                 18

<210> SEQ ID NO 176
<211> LENGTH: 18
<212> TYPE: DNA
<213> ORGANISM: Homo sapiens

<400> SEQUENCE: 176
tcgcagctac cgcagtgt                                                 18

<210> SEQ ID NO 177
<211> LENGTH: 18
<212> TYPE: DNA
<213> ORGANISM: Homo sapiens

<400> SEQUENCE: 177
gcagctaccg cagtgtgg                                                 18

<210> SEQ ID NO 178
<211> LENGTH: 20
<212> TYPE: DNA
<213> ORGANISM: Homo sapiens

<400> SEQUENCE: 178
accacggctc ccactgcagc                                               20

<210> SEQ ID NO 179
<211> LENGTH: 20
<212> TYPE: DNA
<213> ORGANISM: Homo sapiens

<400> SEQUENCE: 179
cacggctccc actgcagcag                                               20
```

<210> SEQ ID NO 180
<211> LENGTH: 20
<212> TYPE: DNA
<213> ORGANISM: Homo sapiens

<400> SEQUENCE: 180
ggctcccact gcagcagctc					20

<210> SEQ ID NO 181
<211> LENGTH: 20
<212> TYPE: DNA
<213> ORGANISM: Homo sapiens

<400> SEQUENCE: 181
ccactgcagc agctcggggg					20

<210> SEQ ID NO 182
<211> LENGTH: 20
<212> TYPE: DNA
<213> ORGANISM: Homo sapiens

<400> SEQUENCE: 182
tgcagcagct cgggggaccc					20

<210> SEQ ID NO 183
<211> LENGTH: 20
<212> TYPE: DNA
<213> ORGANISM: Homo sapiens

<400> SEQUENCE: 183
gggggacccc gctgagtaca					20

<210> SEQ ID NO 184
<211> LENGTH: 20
<212> TYPE: DNA
<213> ORGANISM: Homo sapiens

<400> SEQUENCE: 184
cccgctgagt acaacctgcg					20

<210> SEQ ID NO 185
<211> LENGTH: 20
<212> TYPE: DNA
<213> ORGANISM: Homo sapiens

<400> SEQUENCE: 185
ctgtgcggga cctgcgggca					20

<210> SEQ ID NO 186
<211> LENGTH: 20
<212> TYPE: DNA
<213> ORGANISM: Homo sapiens

<400> SEQUENCE: 186
cgggacctgc gggcagcctg					20

<210> SEQ ID NO 187
<211> LENGTH: 20
<212> TYPE: DNA
<213> ORGANISM: Homo sapiens

<400> SEQUENCE: 187
cctgcgggca gcctgccgac                                       20